United States Patent [19]

Altermatt

[11] Patent Number: 5,633,355
[45] Date of Patent: May 27, 1997

[54] MONOAZO DISPERSE DYES FROM SELECTED (AROMATIC AMINO) PROPIONATES OR SELECTED (AROMATIC AMINO)BUTYRATES

[75] Inventor: Ruedi Altermatt, Buckten, Switzerland

[73] Assignee: Sandoz Ltd., Basel, Switzerland

[21] Appl. No.: 554,687

[22] Filed: Nov. 7, 1995

Related U.S. Application Data

[63] Continuation of Ser. No. 373,171, Jan. 17, 1995, abandoned.

[30] Foreign Application Priority Data

Jan. 17, 1994 [DE] Germany ............... 44 01 096.6

[51] Int. Cl.$^6$ .................. C09B 29/08; D06P 1/18; D06P 3/40; D06P 3/52
[52] U.S. Cl. ............... 534/761; 534/765; 534/768; 534/769; 534/770; 534/777; 534/804; 8/471; 8/506; 8/532; 8/529; 8/693; 8/918; 8/921; 8/922
[58] Field of Search ............... 534/761, 765, 534/768, 769, 770, 777, 804; 8/471, 506, 529, 532, 693

[56] References Cited

U.S. PATENT DOCUMENTS

| | | | |
|---|---|---|---|
| 3,970,617 | 7/1976 | Bruno | 534/804 |
| 4,210,586 | 7/1980 | Clark et al. | 534/804 X |
| 4,271,071 | 6/1981 | Clark | 534/777 X |
| 4,439,362 | 3/1984 | Koerte | 534/777 X |
| 5,420,254 | 5/1995 | Altermatt et al. | 534/558 |

FOREIGN PATENT DOCUMENTS

| | | | |
|---|---|---|---|
| 2712969 | 10/1978 | Germany | 534/804 |

*Primary Examiner*—Fiona T. Powers
*Attorney, Agent, or Firm*—Robert S. Honor; Carl W. Battle; Carol A. Loeschorn

[57] ABSTRACT

The disperse dyes of formula I $$D-N=N-K-N\begin{matrix}R_3\\ \\ Y-CO-O\text{\textendash}CH(R_4)-CO-O\text{\textendash}_m\\-CH(R_{10})-(CH_2)_n\text{\textendash}O-CH(R_{10})CH_2\text{\textendash}_z R_5\end{matrix}$$

wherein the symbols D, K, $R_{3-5}$, $R_{10}$, m, z, n and Y possess the significances given in claim 1, are eminently suitable for dyeing or printing hydrophobic, fully or semi-synthetic, organic fiber materials.

14 Claims, No Drawings

MONOAZO DISPERSE DYES FROM SELECTED (AROMATIC AMINO) PROPIONATES OR SELECTED (AROMATIC AMINO)BUTYRATES

This is a continuation of application Ser. No. 08/373,171, filed Jan. 17, 1995, now abandoned.

The invention relates to the disperse dyes of the general formula I

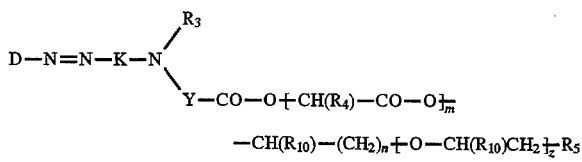

wherein

D signifies a diazo component which is usual with disperse dyes,

K signifies an aromatic radical of formula

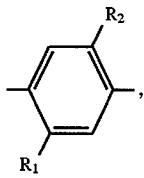  (a)

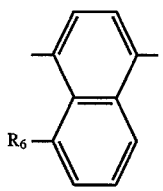  (b)

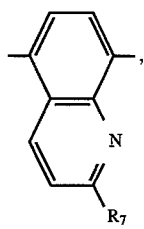  (c)

$R_1$ signifies hydrogen, chlorine, $C_{1-2}$-alkyl, $C_{1-2}$-alkoxy or acylamino, $R_2$ signifies hydrogen, $C_{1-4}$-alkoxy, $C_{1-2}$-alkoxyethoxy, chlorine, bromine, or together with $R_3$ signifies a group of formula —*$CH(CH_3)CH_2C(CH_3)_2$— (*bonded to the nucleus), $R_3$ signifies hydrogen, $C_{1-6}$-alkyl, $C_{3-4}$-alkenyl, chloro- or bromo-$C_{3-4}$-alkenyl, $C_{3-4}$-alkinyl, phenyl-$C_{1-3}$-alkyl, $C_{1-4}$-alkoxycarbonyl-$C_{1-3}$-alkyl, $C_{3-4}$-alkenyloxycarbonyl-$C_{1-3}$-alkyl, $C_{3-4}$-alkinyloxycarbonyl-$C_{1-3}$-alkyl, phenoxy-$C_{2-4}$-alkyl; $C_{2-4}$-alkyl substituted by halogen, cyano, $C_{1-4}$-alkoxy, $C_{1-4}$-alkylcarbonyloxy or $C_{1-4}$-alkoxycarbonyloxy; or a group of formula —$CH_2$—$CH(R_8)CH_2$—$R_9$, $R_4$ signifies hydrogen, phenyl or $C_{1-2}$-alkyl, $R_5$ signifies a radical of formula

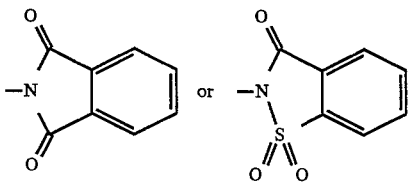

$R_6$ signifies hydrogen or hydroxyl, $R_7$ signifies hydrogen or $C_{1-4}$-alkyl, $R_8$ signifies hydroxyl, $C_{1-4}$-alkylcarbonyloxy or $C_{1-4}$-alkoxycarbonyloxy, $R_9$ signifies chlorine, $C_{1-4}$-alkoxy, phenoxy, allyloxy or $C_{1-4}$-alkylcarbonyloxy, $R_{10}$ signifies hydrogen or $C_{1-4}$-alkyl, Y signifies $C_{2-3}$-alkylene, m and z independently signify zero or 1 and n signifies a number from 1 to 5, with the proviso that, if K is a radical of formula b or c, $R_3$ only signifies hydrogen One group of preferred dyestuffs of formula I corresponds to the general formula Ia

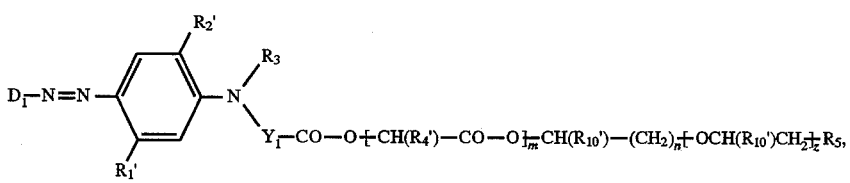  (Ia)

wherein $D_1$ is 3-phenyl-1,2,4-thiadiazolyl or corresponds to one of the following formulae:

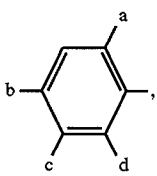

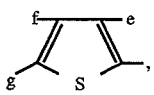

-continued

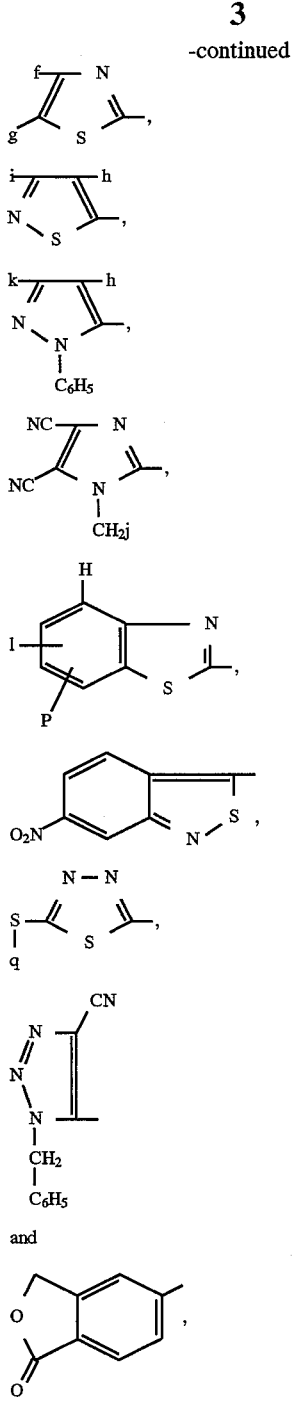

wherein a signifies hydrogen, chlorine, bromine, cyano, nitro-, $C_{1-4}$-alkoxycarbonyl, $C_{1-3}$-alkylsulphonyl, preferably hydrogen, chlorine, cyano or nitro, b signifies chlorine, bromine, nitro, methyl, $C_{1-2}$-alkylsulphonyl, $C_{1-4}$-alkylcarbonyl, aminosulphonyl, mono- or di-$C_{1-4}$-alkylaminosulphonyl, phenylaminosulphonyl, $C_{1-4}$-alkoxycarbonyl, aminocarbonyl, mono- or di-$C_{1-4}$-alkylaminocarbonyl, phenylaminocarbonyl, phenylazo, benzyloxycarbonyl, tetrahydrofurfuryl-2-oxycarbonyl, $C_{3-4}$-alkenyloxycarbonyl, $C_{3-4}$-alkinyloxycarbonyl or phenoxycarbonyl, c signifies hydrogen or chlorine, or if d is hydrogen, also thiocyano, d signifies hydrogen, chlorine, bromine or cyano, e signifies nitro, $C_{1-4}$-alkylcarbonyl, $C_{1-4}$-alkoxycarbonyl, cyano, aminocarbonyl, mono- or di-$C_{1-4}$-alkylaminocarbonyl, f signifies hydrogen, chlorine, bromine, $C_{1-2}$-alkyl or phenyl, g signifies nitro, cyano, formyl, dicyanovinyl or a group of formula —CH=CH—NO$_2$, —CH=C(CN)CO—OC$_{1-4}$-alkyl, H$_5$C$_6$—N=N— or 3- or 4-NO$_2$—C$_6$H$_4$—N=N—, h signifies cyano or $C_{1-4}$-alkoxycarbonyl, i signifies $C_{1-4}$-alkyl or phenyl, j signifies —CN, —CH=CH$_2$ or phenyl, k signifies $C_{1-4}$-alkyl, l signifies hydrogen, chlorine, bromine, cyano, thiocyano, nitro, $C_{1-4}$-alkoxycarbonyl or di-$C_{1-4}$-alkylaminosulphonyl, p signifies hydrogen, chlorine or bromine and q signifies $C_{1-4}$-alkyl, $C_{1-4}$-alkoxycarbonyl-$C_{1-4}$-alkylene or $C_{1-4}$-alkylene-COOCH$_2$CF$_3$, whereby the phenyl nuclei of these substituents may bear one or two substituents from the series chlorine, bromine, methyl or $C_{1-2}$-alkoxy, $R_1'$ signifies hydrogen, $C_{1-2}$-akyl, chlorine or acylamino, $R_2'$ signifies hydrogen, chlorine, $C_{1-2}$-alkoxy, $C_{1-2}$-alkoxyethoxy, or with $R_3$, a group of formula —CH(CH$_3$)CH$_2$C(CH$_3$)$_2$—, $R_3$ and $R_5$ have the significances given above, $R_4'$ and $R_{10}'$ independently signify hydrogen or $C_{1-2}$-alkyl and $Y_1$ signifies a group of formula —CH$_2$CH$_2$— or —CH(CH$_3$)CH$_2$— m and z independently signify zero or 1 and n signifies a number from 1 to 5.

Particularly preferred disperse dyes correspond to formula Ib

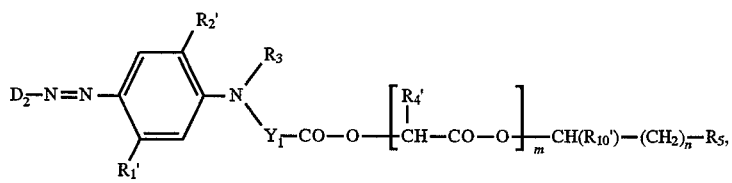

(Ib)

wherein $D_2$ signifies the radical of a diazo component from the series 2,6-dicyano-4-chloro-, -4-bromo-, -4-methyl- or -4-nitrophenyl, 2,4-dinitro-6-chloro-, -6-bromo- or -6-cyanophenyl, 2-chloro- or 2-bromo-4-nitro-6-cyanophenyl, 2,4-dinitrophenyl, 2,6-dichloro- or 2,6-dibromo-4-nitrophenyl, 2-chloro-4-nitro-6-bromophenyl, 2-chloro-, 2-bromo- or 2-cyano-4-nitrophenyl, 2,4-dinitro-5-chlorophenyl or -5-thiocyanophenyl, 2,4-dinitro-5,6-dichlorophenyl, 2,5-dichloro-4-nitrophenyl, 4-nitrophenyl, 4-phenylazophenyl, 4-$C_{3-4}$-alkenyloxycarbonylphenyl, 4-$C_{3-4}$-alkinyloxycarbonylphenyl, 4-$C_{1-4}$-alkoxycarbonylphenyl, 2-$C_{1-4}$-alkoxycarbonyl-4-nitrophenyl, 4-phenoxycarbonylphenyl, 4-benzyloxycarbonylphenyl, 4-(tetrahydrofurfuryl-2'-oxycarbonyl)-phenyl, 3,5-dicyano-4-chloro-thienyl-2, 3,5-dicyano-thienyl-2, 3-cyano-5-nitro-thienyl-2, 3-acetyl-5-nitro-thienyl-2, 3,5-dinitro-thienyl-2, 3-($C_{1-4}$-alkoxycarbonyl)-5-nitro-thienyl-2, 5-phenylazo-3-cyanothienyl-2, 5-phenylazo-3-cyano-4-methyl-thienyl-2, 5-nitro-thiazolyl-2, 5-nitrobenzisothiazolyl-3, 3-methyl-4-cyano-isothiazolyl-5, 3-phenyl-1,2,4-thiadiazolyl-2, 5-($C_{1-2}$-alkylmercapto)-1,3,4-thiadiazolyl-2, 3-$C_{1-2}$-alkoxycarbonylethylmercapto-1,2,4-thiadiazolyl-5, 1-cyanomethyl-4,5-dicyano-imidazolyl-2, 6-nitrobenzothiazolyl-2, 5-nitrobenzothiazolyl-2, 6-thiocyanobenzothiazolyl-2, 6-chlorobenzothiazolyl-2, (5),6,(7)-dichlorobenzothiazolyl-2, phthalidyl-5 or of formula Cl—⧸═⧹—CN       Cl—⧸═⧹—N
B=CH    S    or    B=CH    S    ⫽ in which B signifies oxygen or a group of formula

=C(CN)$_2$,  =CHNO$_2$  or  =C⟨CN / CO—O—C$_{1-4}$-alkyl and the symbols $R_1'$, $R_2'$, $R_3$, $R_4'$, $R_5$, $R_{10}'$, m, n and $Y_1$ are defined as above.

Furthermore, particular preference is given to the disperse dyes of formula Ib, wherein $D_2$ signifies the radical of a diazo component from the series 2,6-dicyano-4-chloro-, -4-bromo, -4-methyl or -4-nitro-phenyl, 2,4-dinitro-6-chloro-, -6-bromo- or -6-cyanophenyl, 2-chloro- or 2-bromo-4-nitro-6-cyanophenyl, 2,4-dinitrophenyl, 2,6-dichloro- or 2,6-dibromo-4-nitrophenyl, 2-chloro-4-nitro-6-bromophenyl, 2-chloro-, 2-bromo- or 2-cyano-4-nitrophenyl, 2,4-dinitro-5-chlorophenyl or -5-thiocyanophenyl, 2,4-dinitro-5,6-dichlorophenyl, 2,5-dichloro-4-nitrophenyl, 4-nitrophenyl, phthalidyl-5, or of formula Cl—⧸═⧹—CN       Cl—⧸═⧹—N
B=HC    S    or    B=HC    S    ⫽ in which B signifies oxygen or a group of formula

=C(CN)$_2$,  or  =C⟨CN / CO—O—C$_{1-4}$-alkyl and the symbols $R_1'$, $R_2'$, $R_3$, $R_4'$, $R_5$, $R_{10}'$, m, n and $Y_1$ are defined as above.

Furthermore, particular preference is given to the disperse dyes of formula Ib, wherein $D_2$ signifies a diazo component from the series 2,4-dinitro-6-chloro-, -6-bromo- or -6-cyanophenyl, 2,4-dinitro-5-chloro- or -5-thiocyanophenyl or 2,4-dinitro-5,6-dichlorophenyl, $R_1'$ signifies $C_{1-2}$-alkylcarbonylamino, $R_2'$ signifies $C_{1-2}$-alkoxy or $C_{1-2}$-alkoxyethoxy, $R_3$ signifies hydrogen, $C_{1-4}$-alkyl, cyanoethyl, $C_{1-2}$-alkoxyethyl, $C_{3-4}$-alkenyl, chlorallyl, $C_{3-4}$-alkinyl, $C_{1-2}$-alkoxycarbonylmethyl, allyloxycarbonylmethyl or propargyloxycarbonylmethyl, $R_4'$ signifies hydrogen or methyl, $R_5$ signifies a radical of formula

[phthalimido structure]  or  [benzisothiazole-1,1-dioxide structure]

$R_{10}'$ signifies hydrogen or methyl, $Y_1$ signifies a group of formula —CH$_2$CH$_2$— or —CH(CH$_3$)CH$_2$— m signifies nill or 1, and n signifies a number from 1 to 5.

Also preferred are the disperse dyes of formula Ib, wherein $D_2$ signifies 2,4-dinitro-6-chloro- or -6-bromophenyl, $R_1'$ signifies $C_{1-2}$-alkylcarbonylamino, $R_2'$ signifies methoxy or ethoxy, $R_3$ signifies hydrogen, allyl, chlorallyl or propargyl, $R_5$ signifies a radical of formula

[phthalimido structure]  or  [benzisothiazole-1,1-dioxide structure]

$R_{10}'$ signifies hydrogen or methyl, $Y_1$ signifies 1,2-ethylene, m signifies zero or 1, and n signifies a number from 1 to 5.

Further preference is also given to the disperse dyes of formula I, wherein

D signifies a diazo component from the series 4-nitrophenyl, 4-nitro-2-ethylsulphonylphenyl, 4-nitro-2-methylsulphonylphenyl, 4-methoxycarbonylphenyl, phthalidyl-5, 4-ethoxycarbonylphenyl, 2-chloro-4- nitrophenyl, 2,6-dichloro-4-nitrophenyl, 2-bromo-4-nitro-6-chlorophenyl or 2-cyano-4-nitrophenyl, K signifies a radical of formula a $R_1$ signifies hydrogen, methyl, acylamino or chlorine, $R_2$ signifies hydrogen, $R_3$ signifies $C_{1-4}$-alkyl, $C_{3-4}$-alkenyl, chlorallyl, benzyl, cyanoethyl, $C_{1-2}$-alkoxyethyl, $C_{1-4}$-alkylcarbonyloxyethyl, $C_{1-2}$-alkoxycarbonylethyl or $C_{1-4}$-alkoxycarbonyloxyethyl, $R_4$ and $R_{10}$ independently signify hydrogen or $C_{1-2}$-alkyl, $R_5$ signifies a radical of formula

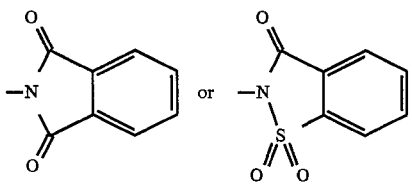

Y signifies a group of formula —$CH_2CH_2$— or —CH($CH_3$)$CH_2$— m and z independently signify zero or 1, and n signifies a number from 1 to 5.

One further group of especially preferred disperse dyes corresponds to formula Ib, wherein $D_2$ signifies a diazo component from the series 4-nitrophenyl, 2-chloro-4-nitrophenyl, 2-bromo-4-nitrophenyl, 2,6-dichloro-4-nitrophenyl, 2-chloro-4-nitro-6-bromophenyl, 2-cyano-4-nitrophenyl, $R_1'$ signifies hydrogen or methyl, $R_2'$ signifies hydrogen, $R_3$ signifies $C_{1-4}$-alkyl, $R_4'$ signifies hydrogen or methyl, $R_5$ signifies a radical of formula

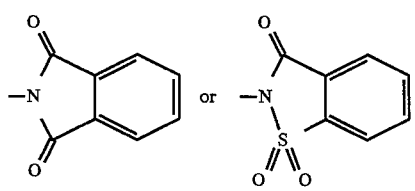

$R_{10}'$ signifies hydrogen, $Y_1$ signifies 1,2-ethylene, m signifies zero or 1, and n signifies the number 1.

The diazo components may be all mono- to bi-nuclear, carbocyclic or heterocyclic organic radicals of aromatic character, which may bear substituents that are conventional in the case of disperse dyes. Water-solubilizing substituents are excluded in particular, that is especially sulphonic acid groups. The diazo components may also be radicals of monoazo compounds. Examples of diazo components are: phenyl, thienyl, thiazolyl, isothiazolyl, thiadiazolyl, pyrazolyl, imidazolyl, triazolyl, benzothiazolyl or benzisothiazolyl radicals, which preferably bear substituents.

The substituents on these nuclei may be in particular halogen atoms, especially chlorine, bromine or iodine atoms, nitro, cyano, thiocyano, hydroxyl, alkyl, alkoxy, phenyl, phenoxy and acyl groups, as well as especially also on the thienyl or thiazolyl diazo components, formyl and radicals of formulae —CH=CH—$NO_2$, —CH=C(CN)$_2$ and —CH=C(CN)acyl.

Preferred acyl groups correspond to formula E—Y— or E'—Z—, in which

E signifies a hydrocarbon radical which may bear the above-mentioned substituents and/or may contain hetero atoms, preferably an optionally substituted alkyl or phenyl radical, Y signifies a radical —O—CO—, —$SO_2$— or —O—$SO_2$—, E' signifies a hydrogen atom or E, Z signifies —CO—, —NE"—CO— or —NE"—$SO_2$— (E" is only bonded to the nitrogen atom), and E" signifies hydrogen or E.

If not otherwise stated, all the said alkyl and alkoxy groups contain 1 to 8, especially 1 to 4 carbon atoms. They may be straight-chain or branched, and bear as substituents e.g. halogen atoms, preferably fluorine or chlorine atoms, hydroxy, alkoxy, phenyl, phenoxy, cyano, thiocyano, acyl, acyloxy or acylamino groups. The intermediate element Y is preferably a group of formula

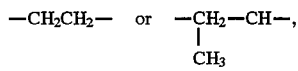

especially —$CH_2CH_2$—.

All the said phenyl radicals (also phenoxy and phenylazo radicals) may be further substituted, e.g. by halogen atoms (preferably chlorine or bromine atoms), alkyl, alkoxy, nitro, cyano, thiocyano, acyl, acyloxy or acylamino groups.

If not indicated to the contrary, all alkyl, alkylene and alkenyl radicals are straight-chain.

Production of the new dyestuffs of formula I is characterized in that a diazotised amine of formula II

D—$NH_2$ (II)

is coupled with a compound of formula III

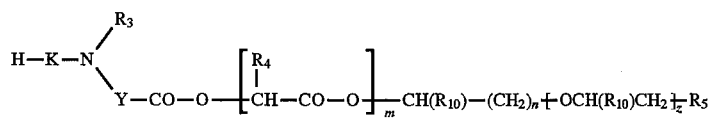

Diazotisation and coupling are effected according to generally known methods.

The compounds of formulae II and III are known, or may be easily produced from known compounds according to methods known to a person skilled in the art.

Dyestuffs of formula I in which D corresponds to the formula

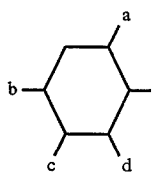

where a and/or d are a cyano radical, can also be prepared by cyano-exchange from the corresponding halogen substituted dyestuffs, such a method is known to the skilled person.

From an aqueous suspension, the new dyestuffs of formula I are absorbed in an excellent manner on textile material consisting of fully synthetic or semi-synthetic, hydrophobic, high molecular weight organic matter. They are especially suitable for dyeing or printing textile material consisting of linear, aromatic polyesters, as well as cellulose-2½-acetate and cellulose triacetate.

Dyeing or printing are effected in accordance with known processes, e.g. those described in French Patent Specification no. 1.445.371.

The dyeings obtained have good all-round fastnesses; apart from the good fastness to thermomigration, also notable are the light fastness, thermofixation fastness and pleating fastness, as well as the excellent wet fastness, following thermal fixation (especially the M&S C4A Co domestic wash).

They are also especially suitable for thermo transfer printing processes.

In the following examples, the parts and percentages are by weight. The temperatures are given in degrees celsius.

EXAMPLE 1

16.3 parts of 2-amino-5-nitrobenzonitrile are stirred into 100 parts of cold sulphuric acid (93%) and mixed at 0° to 5° over the course of 30 minutes with 32 parts of nitrosylsulphuric acid (40%). Stirring continues for 3 to 4 hours at 0° to 5° and then the diazonium salt solution obtained is poured whilst stirring into a mixture of 35.2 parts of 3-(N-methyl-N-phenylamino)-propionic acid-2'-N-phthalimidoethylester, 100 parts of glacial acetic acid, 2 parts of amidosulphonic acid, 200 parts of water and 500 parts of ice. The precipitated dyestuff is filtered off, washed with water until free from acid and dried in a vacuum at 60°. The resultant dyestuff corresponds to formula

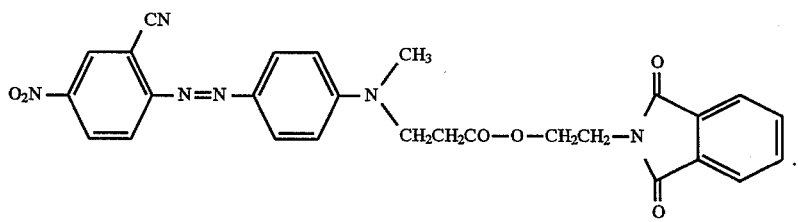

It dyes polyester fibre material in ruby-red shades with excellent fastness, in particular very good wet fastness after thermal fixing, and is eminently suitable for the modern rapid-dyeing processes, for example the $^R$Foron-RD process. $\lambda_{max.}=533$ nm (DMF).

EXAMPLE 2

The process is as described in example 1, but the 35.2 parts of 3-(N-methyl-N-phenylamino)-propionic acid-2'-N-phthalimidoethylester are replaced by 42.4 parts of 3-(N-ethyl-N-phenylamino)-propionic acid-(2'-N-phthalimidoethoxycarbonyl)methylester. The resultant dyestuff corresponds to formula

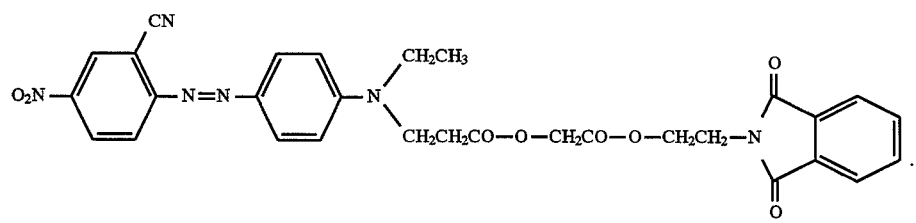

It dyes polyester fibre materials in ruby-red shades with excellent fastnesses, in particular very good wet fastness, after thermal fixing. $\lambda_{max.}=537$ nm (DMF).

EXAMPLE 3

The process is as described in example 1, but the 35.2 parts of 3-(N-methyl-N-phenylamino)-propionic acid-2'-N-phthalimidoethylester are replaced by 38.8 parts of 3-(N-methyl-N-phenylamino)-propionic acid-2'-N-o-sulphobenzimidoethylester. The resultant dyestuff corresponds to formula

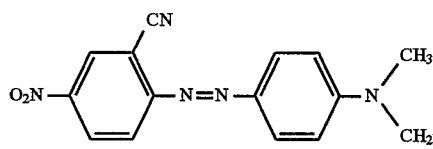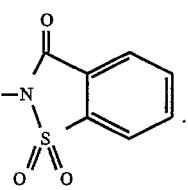

It dyes polyester fibre materials in ruby-red shades with excellent fastness, in particular very good wet fastness, after thermal fixing, and is eminently suitable for the modern rapid-dyeing processes, for example the ᴿForon-RD process. $\lambda_{max.}=534$ nm (DMF).

EXAMPLE 4

20.7 parts of 1-amino-2,6-dichloro-4-nitrobenzene are stirred into 100 parts of sulphuric acid (93%) and mixed at 30° over the course of one hour with 32 parts of nitrosylsulphuric acid (40%). Stirring is effected for 2–3 hours at 30°–32°, and then the diazonium salt solution obtained is added in drops whilst stirring to a mixture of 35.2 parts of 3-(N-methyl-N-phenylamino)-propionic acid-2'-N-phthalimidoethylester, 100 parts of glacial acetic acid, 2 parts of amidosulphonic acid, 200 parts of water and 500 parts of ice. The precipitated dyestuff is filtered off, washed with water until free from acid, and dried in a vacuum at 60°. It corresponds to formula

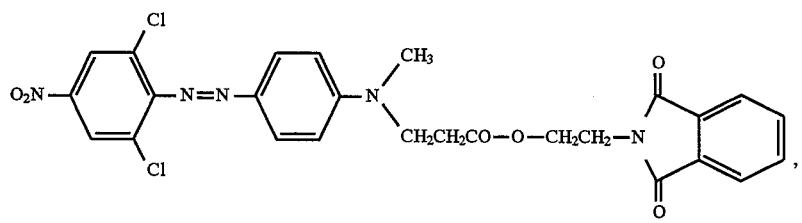

and dyes polyester fibre material in yellow-brown shades with excellent fastness, in particular very good wet fastness, after thermal fixing.

$\lambda_{max.}$(DMF)=439 nm.

methoxyphenylamino)-propionic acid-2'-N-o-sulphobenzimidoethylester, 100 parts of glacial acetic acid and 300 parts of ice/water. The precipitated dyestuff is filtered off, washed with water until free from acid, and dried in a vacuum at 60°. The dyestuff obtained, with $\lambda_{max.}=598$ nm (DMF), corresponds to formula

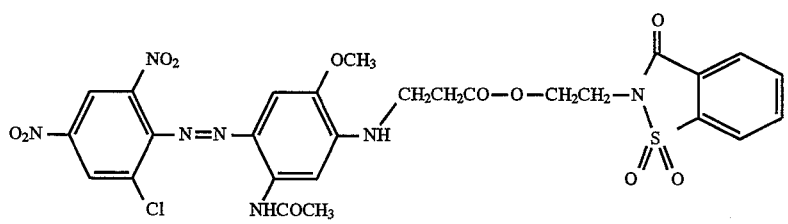

and dyes polyester materials, resp. polyester/cotton mixed fabric, in marine-blue shades with excellent fastness, in particular very good wet fastness, after thermal fixing.

EXAMPLE 6

20.8 parts of 2-cyano-4,6-dinitroaniline are stirred into 150 parts of sulphuric acid (93%) at 0° to 5° and mixed over

EXAMPLE 5

21.8 parts of 2-chloro-4,6-dinitroaniline are stirred into 150 parts of 93% sulphuric acid at 15°–20°, and mixed over the course of 30 minutes with 32 parts of 40% nitrosylsulphuric acid. The mixture is stirred for 2–3 hours in an ice bath, and the diazonium salt solution is continuously poured into a mixture of 46.1 parts of 3-N-(5"-acetylamino-2"- the course of 30 minutes with 32 parts of nitrosylsulphuric acid (40%). Stirring continues for 2 to 3 hours at 0° to 5° and then the diazonium salt solution obtained is poured whilst stirring into a mixture of 39.6 parts of 3-[N-methyl-N-(5"-methyl-2"-methoxyphenyl)amino]-propionic acid-2'-N-phthalimidoethylester, 100 parts of glacial acetic acid and 300 parts of ice/water. The precipitated dyestuff is filtered off, washed with water until free from acid and dried in a vacuum at 60°. The resultant dyestuff having a $\lambda_{max}$=613 nm (DMF) corresponds to formula

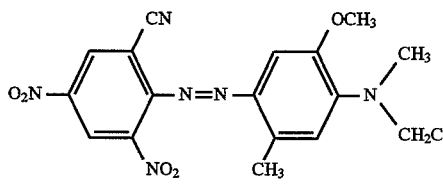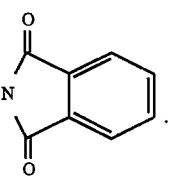

It dyes polyester fibre material in blue shades with excellent fastness, in particular very good wet fastness after thermal fixing, and is eminently suitable for the modern rapid-dyeing processes, for example the $^R$Foron-RD process.

EXAMPLE 7

20.8 parts of 2-cyano4,6-dinitroaniline are stirred into 150 parts of sulphuric acid (93%) at 0° to 5° and mixed over the course of 30 minutes with 32 parts of nitrosylsulphuric acid (40%). Stirring continues for 2 to 3 hours at 0° to 5° and then the diazonium salt solution obtained is poured whilst stirring into a mixture of 45.2 parts of 3-[N-ethyl-N-(3'-methylphenyl)amino]-propionic acid-(3"-N-phthalimido-n-propoxycarbonyl)-methylester, 100 parts of glacial acetic acid, and 300 parts of ice/water. The precipitated dyestuff is filtered off, washed with water until free from acid and dried in a vacuum at 60°. The resultant dyestuff having a $\lambda_{max}$= 590 nm (DMF) corresponds to formula thermal fixing, and is eminently suitable for the modern rapid-dyeing processes, for example the $^R$Foron-RD process.

Analogously to the method of Example 1 by using the corresponding starting materials further compounds of formula I may be obtained.

These compounds correspond to the formulae given hereinbelow, for which the particular variants are listed in the following tables. They dye polyester fibers in the indicated shades with excellent fastnesses, in particular very good wet fastness after thermal fixing. In the following tables "do." signifies ditto, i.e. same as the previous entry, PES stands for polyester fibres and DK stands for diazo component radical.

The dyestuffs of the following Table I correspond to formula

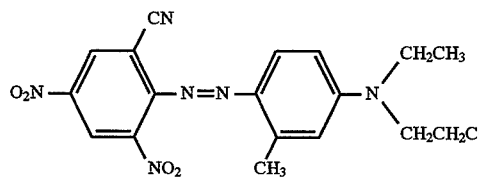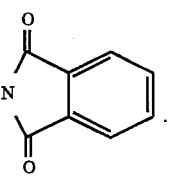

It dyes polyester fibre material in ruby-red shades with excellent fastness, in particular very good wet fastness after

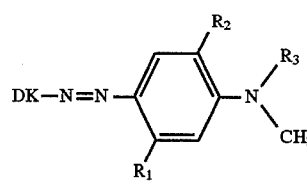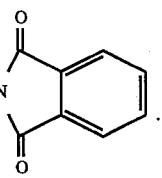

TABLE 1

| exp. no. | DK | R₁ | R₂ | R₃ | Shade on PES |
|---|---|---|---|---|---|
| 8 | 4-nitro-2-(ethylsulfonyl)phenyl (O₂N–C₆H₃–SO₂CH₂CH₃) | H | H | —C$_2$H$_5$ | ruby |
| 9 | " | H | H | —CH$_3$ | " |
| 10 | " | H | H | —CH$_2$CH$_2$CN | red |
| 11 | 4-nitro-2-(methoxycarbonyl)phenyl (O₂N–C₆H₃–COOCH$_3$) | H | H | —CH$_3$ | " |
| 12 | 4-nitro-2-chlorophenyl (O₂N–C₆H₃–Cl) | H | H | —C$_2$H$_4$CN | scarlet |
| 13 | 2,5-dichloro-4-nitrophenyl | H | H | " | " |
| 14 | 4-nitro-2-chlorophenyl | —NHCOCH$_3$ | H | " | red |
| 15 | " | " | —Cl | H | scarlet |
| 16 | 4-nitro-2-cyanophenyl (O₂N–C₆H$_3$–CN) | " | " | H | ruby |
| 17 | 4-nitro-2-(methylsulfonyl)phenyl (O₂N–C₆H$_3$–SO$_2$CH$_3$) | H | H | —CH$_3$ | " |
| 18 | 2,5-dichloro-4-nitrophenyl | H | H | —CH$_2$CH=CH$_2$ | yellow-brown |
| 19 | 2,4-dichloro-... (O₂N–C₆H$_3$–Cl, Cl) | H | H | —C$_4$H$_9$ | " |

TABLE 1-continued
| exp. no. | DK | $R_1$ | $R_2$ | $R_3$ | Shade on PES |
|---|---|---|---|---|---|
| 20 | 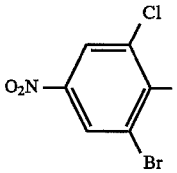 | H | H | —$CH_2CH$=$CH_2$ | yellow-brown |
| 21 | 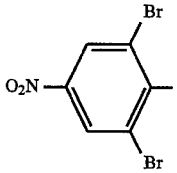 | H | H | " | " |
| 22 | 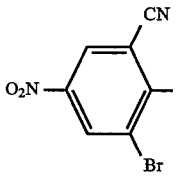 | —NHCOCH$_3$ | H | —$C_2H_5$ | bluish-violet |
| 23 | 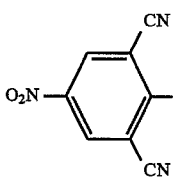 | —CH$_3$ | H | —$C_4H_9$ | reddish blue |
| 24 | " | —NHCOCH$_3$ | H | —$C_3H_7$ | blue |
| 25 | " | —NHCOC$_2$H$_5$ | H | " | " |
| 26 | " | —NHCOCH$_3$ | H | —$C_2H_5$/—$C_3H_7$ (1:1) | " |
| 27 | 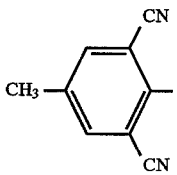 | —CH$_3$ | H | —$C_2H_5$ | scarlet |
| 28 | 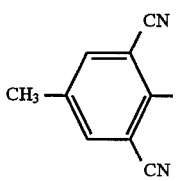 | —NHCOC$_2$H$_5$ | H | $C_2H_5$ | bluish red |
| 29 | " | —NHSO$_2$CH$_3$ | H | $C_2H_5$/$C_3H_7$ (1:1) | red |
| 30 | 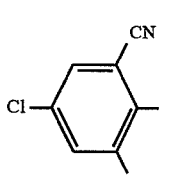 | —NHCOC$_2$H$_5$ | H | " | ruby |
| 31 | 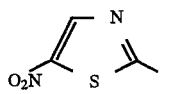 | —CH$_3$ | H | —$C_4H_9$ | bluish violet |

TABLE 1-continued

| exp. no. | DK | $R_1$ | $R_2$ | $R_3$ | Shade on PES |
|---|---|---|---|---|---|
| 32 | H3C—⫽—CN / N—S (methyl) | H | H | —CH₃ | bluish red |
| 33 | " | —CH₃ | H | —C₂H₅ | violet |
| 34 | H3C—⫽—CN / N—S | —NHCOCH₃ | H | —C₂H₄CN | bluish red |
| 35 | H3C—⫽—CN / N—N(C₆H₅) | —CH₃ | H | —C₂H₅ | scarlet |
| 36 | " | —NHCOC₂H₅ | H | " | red |
| 37 | H5C6—⫽—N / N—S | H | H | —C₂H₅ | scarlet |
| 38 | " | —CH₃ | H | " | red |
| 39 | " | —NHCOCH₃ | H | " | ruby |
| 40 | " | " | H | —C₂H₄CN | red |
| 41 | NC,NC—⫽—N / N(CH₂CN) | —CH₃ | H | —C₄H₉ | bluish red |
| 42 | O₂N-benzothiazole | " | H | —C₂H₅ | dark blue |
| 43 | O₂N-benzothiazole | —NHCOCH₃ | H | —C₂H₅/C₃H₇ (1:1) | greenish blue |
| 44 | O₂N—thiophene—NO₂ | H | H | —C₂H₅ | blue |
| 45 | " | —CH₃ | H | " | greenish blue |
| 46 | " | H | H | —C₂H₄OCOCH₃ | reddish blue |
| 47 | " | —NHCOCH₃ | H | —C₂H₅ | bluish green |
| 48 | O₂N—thiophene—COCH₃ | —CH₃ | H | —C₄H₉ | reddish blue |
| 49 | O₂N—thiophene—COOC₂H₅ | " | H | —C₂H₅ | reddish navy blue |
| 50 | H5C6—N=N—thiophene—CN | H | H | " | dark blue |

TABLE 1-continued

| exp. no. | DK | R₁ | R₂ | R₃ | Shade on PES |
|---|---|---|---|---|---|
| 51 | H₅C₆—N=N-[thiophene with H₃C, CN, CH₃] | H | H | —C₂H₅ | dark blue |
| 52 | O₂N—C₆H₄—N=N-[thiophene with CN, CH₃] | H | H | —C₂H₅ | greenish navy blue |
| 53 | 2,4-dinitrophenyl | —NHCOCH₃ | H | —CH₂C≡CH | red |
| 54 | " | " | H | —C₂H₅ | bluish red |
| 55 | H₅C₆-[thiazole with NC, CH₃] | H | H | —C₂H₅ | violet |
| 56 | benzothiazole with NCS | H | H | —C₂H₄CN | red |
| 57 | [thiophene with H₃C, CN, NC, CH₃] | —CH₃ | H | —C₂H₅ | violet |
| 58 | [thiophene with H₃C, CN, NC, CH₃] | " | H | —CH₃ | violet |
| 59 | benzothiazole with O₂N | —CH₃ | H | " | ruby |
| 60 | " | H | H | —C₂H₅ | red |
| 61 | 2-NO₂,4-NO₂,6-CN-phenyl | —NHCOC₂H₅ | H | " | blue |
| 62 | " | —NHCOCH₃ | H | " | " |
| 63 | " | " | H | —C₂H₅—/C₃H₇ (1:1) | " |
| 64 | 2-NO₂,4-NO₂,6-Br-phenyl | —CH₃ | —OCH₃ | —CH₃ | bluish violet |

TABLE 1-continued

| exp. no. | DK | $R_1$ | $R_2$ | $R_3$ | Shade on PES |
|---|---|---|---|---|---|
| 65 | 2-methyl-4-nitro-5-chloro-nitrobenzene (NO₂, NO₂, Cl substituents) | —NHCOCH₃ | H | —C₂H₅ | " |
| 66 | H₅C₂O—CO—CH₂—S—C(=N—N=C)—S (thiadiazole) | —NHCOCH₃ | H | C₂H₅ | red |
| 67 | phthalide (isobenzofuranone) | H | H | —CH₃ | yellow |
| 68 | " | H | H | —C₂H₅ | " |
| 69 | HC≡C—CH₂OC(O)—C₆H₄— | H | H | —CH₃ | " |
| 70 | " | —CH₃ | H | " | " |
| 71 | H₂C=CH—CH₂OC(O)—C₆H₄— | " | H | " | " |
| 72 | " | H | H | " | " |
| 73 | O₂N—C₆H₄— | H | H | " | orange |
| 74 | " | H | H | —C₂H₅ | " |
| 75 | O₂N—C₆H₄— | H | H | —CH₂CH₂O—CO—OCH₃ | orange |
| 76 | " | CH₃ | H | —CH₃ | red |
| 77 | 2-methyl-chloro-nitrobenzene (Cl, O₂N) | H | H | " | " |
| 78 | 2-methyl-bromo-nitrobenzene (Br, O₂N) | H | H | —CH₂CH=CH₂ | " |
| 79 | 2-methyl-cyano-nitrobenzene (CN, O₂N) | H | H | —CH₂CH₂OCOCH₃ | ruby |
| 80 | " | H | H | —CH₂CH₂—O—CO—OCH₃ | " |

TABLE 1-continued

| exp. no. | DK | R₁ | R₂ | R₃ | Shade on PES |
|---|---|---|---|---|---|
| 81 | 4-O₂N, 2-SO₂CH₃, 1-yl (methylphenyl) | H | H | —C₂H₅ | " |
| 82 | 4-O₂N, 2-CN, 1-yl (methylphenyl) | H | H | —C₂H₅ | ruby |
| 83 | 4-O₂N, 2-Cl, 6-Cl phenyl | H | H | " | yellow-brown |

The dyestuffs of the following Table 2 correspond to the formula

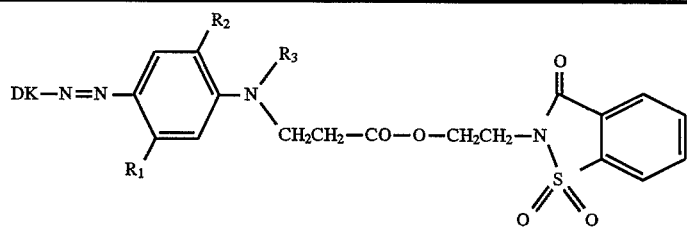

TABLE 2

| exp. no. | DK | R₁ | R₂ | R₃ | Shade on PES |
|---|---|---|---|---|---|
| 84 | 4-O₂N, 2-SO₂CH₂CH₃ phenyl | H | H | —C₂H₅ | ruby |
| 85 | 4-O₂N, 2-CN phenyl | H | H | —C₄H₉ | " |
| 86 | " | H | H | —CH₂CH₂CN | red |
| 87 | 4-O₂N, 2-COOCH₃ phenyl | H | H | —CH₃ | " |
| 88 | 4-O₂N, 2-Cl phenyl | H | H | —C₂H₄CN | scarlet |

TABLE 2-continued
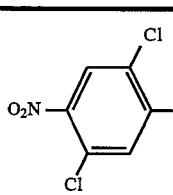
| exp. no. | DK | R₁ | R₂ | R₃ | Shade on PES |
|---|---|---|---|---|---|
| 89 | 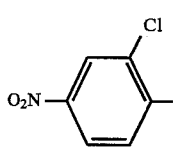 2,5-dichloro-4-nitrophenyl (O₂N, Cl, Cl) | H | H | —C₂H₄CN | scarlet |
| 90 | 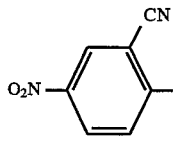 2-chloro-4-nitrophenyl | —NHCOCH₃ | H | " | red |
| 91 | " | " | —Cl | H | scarlet |
| 92 | 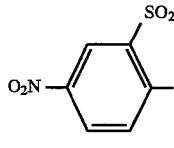 2-cyano-4-nitrophenyl | " | " | H | ruby |
| 93 | 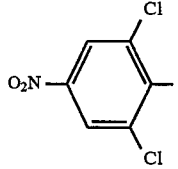 2-methylsulfonyl-4-nitrophenyl | H | H | —C₂H₅ | " |
| 94 | 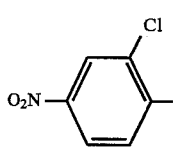 | H | H | —CH₂CH=CH₂ | yellow-brown |
| 95 | 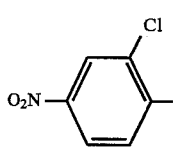 | H | H | —C₄H₉ | yellow-brown |
| 96 | 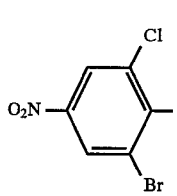 2-bromo-6-chloro-4-nitrophenyl | H | H | —CH₂CH=CH₂ | " |

TABLE 2-continued
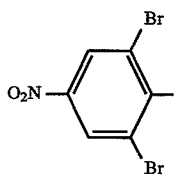
| exp. no. | DK | $R_1$ | $R_2$ | $R_3$ | Shade on PES |
|---|---|---|---|---|---|
| 97 | 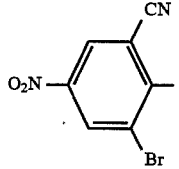 | H | H | " | " |
| 98 | 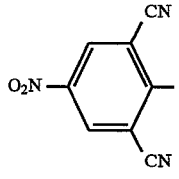 | —NHCOCH$_3$ | H | —C$_2$H$_5$ | bluish violet |
| 99 | 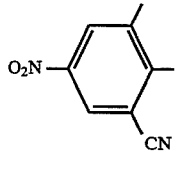 | —CH$_3$ | H | —C$_4$H$_9$ | reddish blue |
| 100 | 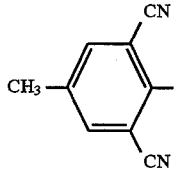 | —NHCOCH$_3$ | H | —C$_3$H$_7$ | blue |
| 101 | " | —NHCOC$_2$H$_5$ | " | " | |
| 102 | " | —NHCOCH$_3$ | H | —C$_2$H$_5$/—C$_3$H$_7$ (1:1) | " |
| 103 | 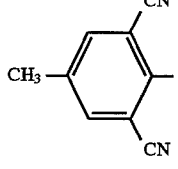 | —CH$_3$ | H | —C$_2$H$_5$ | scarlet |
| 104 | | —NHCOC$_2$H$_5$ | H | —C$_2$H$_5$ | bluish red |
| 105 | " | —NHSO$_2$CH$_3$ | H | C$_2$H$_5$/C$_3$H$_7$ (1:1) | red |

TABLE 2-continued

| exp. no. | DK | R₁ | R₂ | R₃ | Shade on PES |
|---|---|---|---|---|---|
| 106 | 5-Cl-2,4-dicyanophenyl | —NHCOC₂H₅ | H | " | ruby |
| 107 | 3-nitro-2-methylthiazole | —CH₃ | H | —C₄H₉ | bluish violet |
| 108 | 3-methyl-4-cyano-5-methylisothiazole | H | H | —CH₃ | bluish red |
| 109 | " | —CH₃ | H | —C₂H₅ | violet |
| 110 | " | —NHCOCH₃ | H | —C₂H₄CN | bluish red |
| 111 | 3-methyl-4-cyano-5-methyl-1-phenylpyrazole | —CH₃ | H | —C₂H₅ | scarlet |
| 112 | " | —NHCOC₂H₅ | H | " | red |
| 113 | 3-phenyl-5-methylisothiazole | H | H | —C₂H₅ | scarlet |
| 114 | " | —CH₃ | H | " | red |
| 115 | " | —NHCOCH₃ | H | " | ruby |
| 116 | " | " | H | —C₂H₄CN | red |
| 117 | 4,5-dicyano-2-methyl-1-cyanomethylimidazole | —CH₃ | H | —C₄H₉ | bluish red |
| 118 | 5-nitro-benzisothiazole | —CH₃ | H | —C₂H₅ | dark blue |
| 119 | " | —NHCOCH₃ | H | —C₂H₅/C₃H₇ (1:1) | greenish blue |
| 120 | 2,5-dinitro-3-methylthiophene | H | H | —C₂H₅ | blue |
| 121 | " | —CH₃ | H | " | greenish blue |
| 122 | " | H | H | —C₂H₄OCOCH₃ | reddish blue |
| 123 | " | —NHCOCH₃ | H | —C₂H₅ | bluish green |

TABLE 2-continued

Structure: DK—N=N—[phenyl with R2 (top), R1 (bottom)]—N(R3)—CH2CH2—CO—O—CH2CH2—N[benzisothiazole-3-one 1,1-dioxide (saccharin)]

| exp. no. | DK | R₁ | R₂ | R₃ | Shade on PES |
|---|---|---|---|---|---|
| 124 | O₂N–[thiophene]–COCH₃ | –CH₃ | H | –C₄H₉ | reddish blue |
| 125 | O₂N–[thiophene]–COOC₂H₅ | " | H | –C₂H₅ | reddish navy blue |
| 126 | H₅C₆–N=N–[thiophene]–CN | H | H | " | dark blue |
| 127 | H₅C₆–N=N–[thiophene, H₃C, CN] | H | H | –C₂H₅ | dark blue |
| 128 | O₂N–C₆H₄–N=N–[thiophene]–CN | H | H | –C₂H₅ | greenish navy blue |
| 129 | 2,4-dinitrophenyl | –NHCOCH₃ | H | –CH₂C≡CH | red |
| 130 | " | " | H | –C₂H₅ | bluish red |
| 131 | H₅C₆–[thiazole]–CN | H | H | –C₂H₅ | violet |
| 132 | NCS–[benzothiazole] | H | H | –C₂H₄CN | red |
| 133 | H₃C–[thiophene, NC, CN]–CN | –CH₃ | H | –C₂H₅ | violet |
| 134 | H₃C–[thiophene, NC, CN]–CN | –CH₃ | H | –CH₃ | violet |
| 135 | O₂N–[benzothiazole] | –CH | H | " | ruby |
| 136 | " | H | H | –C₂H₅ | red |

TABLE 2-continued

Structure: DK—N=N—[benzene ring with R₂ (top), R₁ (bottom)]—N(R₃)—CH₂CH₂—CO—O—CH₂CH₂—N[saccharin group (benzisothiazole-1,1-dioxide-3-one)]

| exp. no. | DK | R₁ | R₂ | R₃ | Shade on PES |
|---|---|---|---|---|---|
| 137 | 2-methyl-3-cyano-4,6-dinitrophenyl (NO₂ top, O₂N para, CN ortho, CH₃) | —NHCOC₂H₅ | H | " | blue |
| 138 | 2-methyl-3-cyano-4,6-dinitrophenyl | —NHCOCH₃ | H | " | " |
| 139 | " | " | H | —C₂H₅ —/C₃H₇ (1:1) | " |
| 140 | 2-methyl-3-bromo-4,6-dinitrophenyl | " | H | " | bluish violet |
| 141 | 2-methyl-3-chloro-4,6-dinitrophenyl | —NHCOCH₃ | H | —C₂H₅ | bluish violet |
| 142 | H₅C₂O—CO—CH₂—S—[1,3,4-thiadiazol-2-yl] | " | H | " | red |
| 143 | phthalide-5-yl (3H-isobenzofuran-1-one) | H | H | —CH₃ | yellow |
| 144 | " | H | H | —C₂H₅ | " |
| 145 | HC≡C—CH₂OC(O)—(4-phenylene)— | H | H | —CH₃ | " |
| 146 | " | CH₃ | H | " | " |
| 147 | H₂C=CH—CH₂OC(O)—(4-phenylene)— | H | H | " | " |

TABLE 2-continued
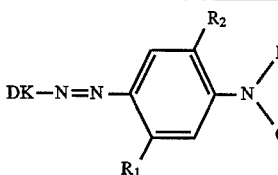
| exp. no. | DK | R₁ | R₂ | R₃ | Shade on PES |
|---|---|---|---|---|---|
| 148 | " | H | H | " | " |
| 149 | 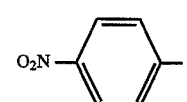 O₂N–⟨⟩– | H | H | —CH₃ | orange |
| 150 | " | H | H | —C₂H₅ | " |
| 151 | " | H | H | —CH₂CH₂O—CO—OCH₃ | ". |
| 152 | " | CH₃ | H | —CH₃ | red |
| 153 | 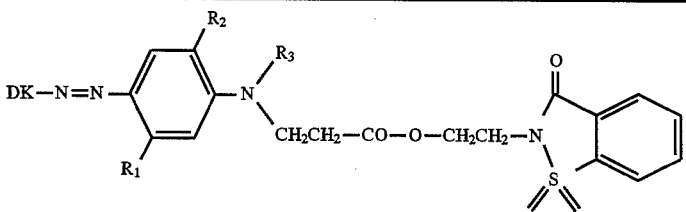 O₂N–⟨Cl⟩– | H | H | " | " |
| 154 | 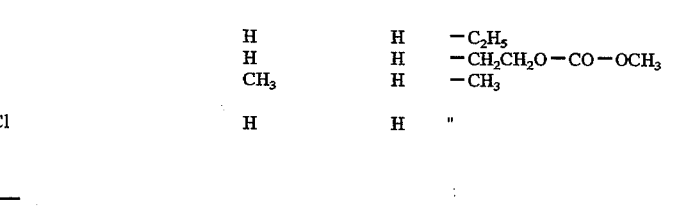 O₂N–⟨Br⟩– | H | H | —CH₂CH=CH₂ | " |
| 155 | 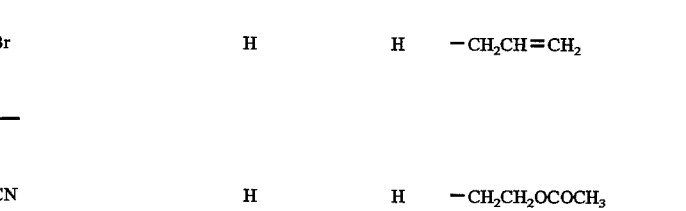 O₂N–⟨CN⟩– | H | H | —CH₂CH₂OCOCH₃ | ruby |
| 156 | " | H | H | —CH₂CH₂—O—CO—OCH₃ | " |
| 157 | 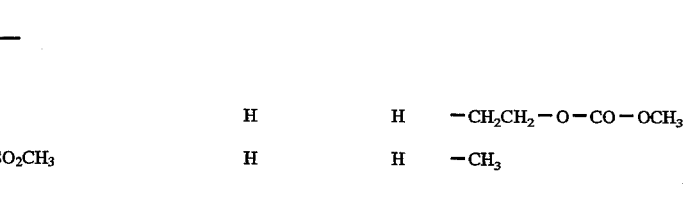 O₂N–⟨SO₂CH₃⟩– | H | H | —CH₃ | ruby |
| 158 | 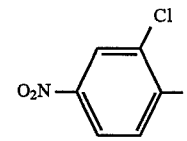 O₂N–⟨CN⟩– | H | H | " | " |
| 159 | 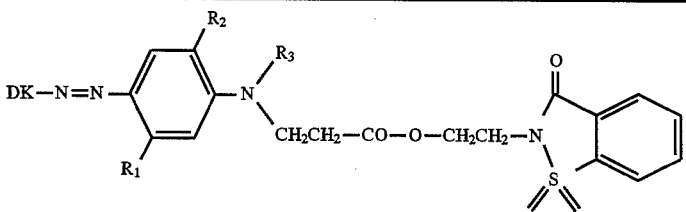 O₂N–⟨Cl,Cl⟩– | H | H | " | yellow brown |
| 160 | " | H | H | —CH₃ | " |
The dyestuffs of the following Table 3 correspond to formula TABLE 3
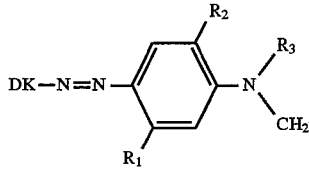
| exp. no. | DK | $R_1$ | $R_2$ | $R_3$ | Shade on PES |
|---|---|---|---|---|---|
| 161 | 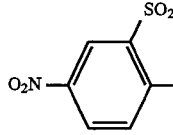 | H | H | $CH_3$ | ruby |
| 162 | 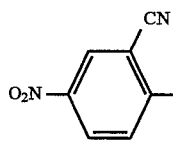 | H | H | $-C_4H_9$ | " |
| 163 | " | H | H | $-CH_2CH_2CN$ | red |
| 164 | 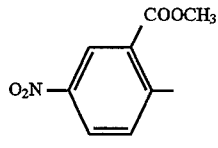 | H | H | $-CH_3$ | " |
| 165 | 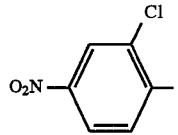 | H | H | $-C_2H_4CN$ | scarlet |
| 166 |  | H | H | $-C_2H_4CN$ | scarlet |
| 167 | 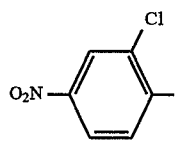 | $-NHCOCH_3$ | H | " | red |
| 168 | " | " | $-Cl$ | H | scarlet |
| 169 | 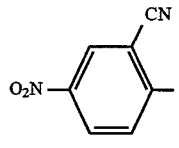 | " | " | H | ruby |
| 170 | 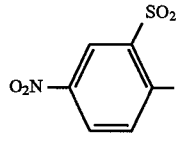 | H | H | $-CH_3$ | " |

TABLE 3-continued
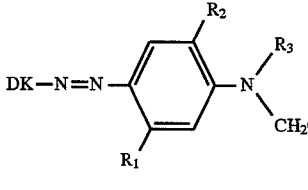
| exp. no. | DK | R₁ | R₂ | R₃ | Shade on PES |
|---|---|---|---|---|---|
| 171 | 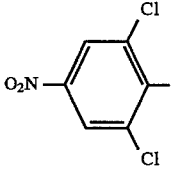 | H | H | —CH₂CH=CH₂ | yellow-brown |
| 172 | 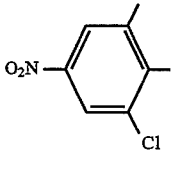 | H | H | —C₄H₉ | yellow-brown |
| 173 | 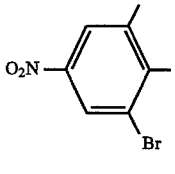 | H | H | —CH₂CH=CH₂ | " |
| 174 | 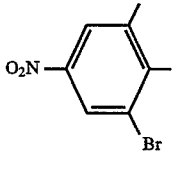 | H | H | " | " |
| 175 | 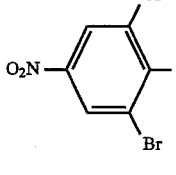 | —NHCOCH₃ | H | —C₂H₅ | bluish violet |
| 176 | 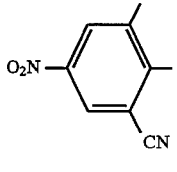 | CH₃ | H | —C₄H₉ | reddish blue |
| 177 | 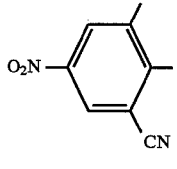 | —NHCOCH₃ | H | —C₃H₇ | blue |
| 178 | " | —NHCOC₂H₅ | H | " | " |
| 179 | " | —NHCOCH₃ | H | —C₂H₅/—C₃H₇ (1:1) | " |

TABLE 3-continued

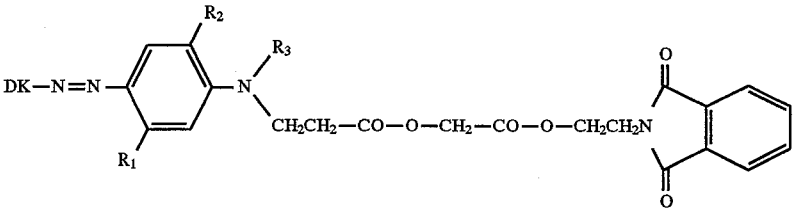

| exp. no. | DK | R₁ | R₂ | R₃ | Shade on PES |
|---|---|---|---|---|---|
| 180 | 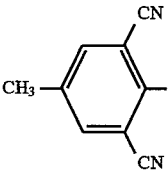 | —CH₃ | H | —C₂H₅ | scarlet |
| 181 | " | —NHCOC₂H₅ | H | " | bluish red |
| 182 | " | —NHSO₂CH₃ | H | C₂H₅/C₃H₇ (1:1) | red |
| 183 | 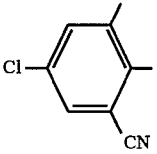 | —NHCOC₂H₅ | H | " | ruby |
| 184 | 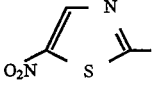 | —CH₃ | H | —C₄H₉ | bluish violet |
| 185 | 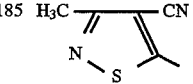 | H | H | —CH₃ | bluish red |
| 186 | " | —CH₃ | H | —C₂H₅ | violet |
| 187 | " | —NHCOCH₃ | H | —C₂H₄CN | bluish red |
| 188 | 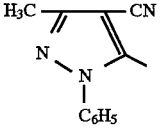 | —CH₃ | H | —C₂H₅ | scarlet |
| 189 | " | —NHCOC₂H₅ | H | " | red |
| 190 | 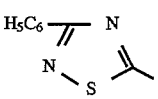 | H | H | —C₂H₅ | scarlet |
| 191 | " | —CH₃ | H | " | red |
| 192 | " | —NHCOCH₃ | H | " | ruby |
| 193 | " | " | H | —C₂H₄CN | red |
| 194 | 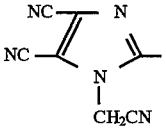 | —CH₃ | H | —C₄H₉ | bluish red |
| 195 | 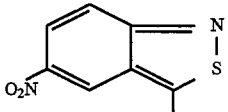 | —CH₃ | H | —C₂H₅ | dark blue |
| 196 | " | —NHCOCH₃ | H | —C₂H₅/C₃H₇ (1:1) | greenish blue |

TABLE 3-continued

Structure: DK—N=N—[phenyl ring with R₂ at position 2, R₁ at position 5]—N(R₃)—CH₂CH₂—CO—O—CH₂—CO—O—CH₂CH₂N(phthalimide)

| exp. no. | DK | R₁ | R₂ | R₃ | Shade on PES |
|---|---|---|---|---|---|
| 197 | 2,4-dinitro-5-methylthiophene (O₂N, NO₂ on thiophene with S) | H | H | —C₂H₅ | blue |
| 198 | " | —CH₃ | H | " | greenish blue |
| 199 | " | H | H | —C₂H₄OCOCH₃ | reddish blue |
| 200 | " | —NHCOCH₃ | H | —C₂H₅ | bluish green |
| 201 | 2-nitro-4-acetyl-5-methylthiophene (O₂N, COCH₃ on thiophene) | —CH₃ | H | —C₄H₉ | reddish blue |
| 202 | 2-nitro-4-ethoxycarbonyl-5-methylthiophene (O₂N, COOC₂H₅) | " | H | —C₂H₅ | reddish navy blue |
| 203 | 5-(phenylazo)-4-cyano-2-methylthiophene (H₅C₆—N=N—, CN) | H | H | " | dark blue |
| 204 | 5-(phenylazo)-3-methyl-4-cyano-2-methylthiophene (H₃C, CN, H₅C₆—N=N—) | H | H | —C₂H₅ | dark blue |
| 205 | 5-(4-nitrophenylazo)-4-cyano-2-methylthiophene (O₂N—C₆H₄—N=N—, CN) | H | H | —C₂H₅ | greenish navy blue |
| 206 | 2,4-dinitrophenyl (NO₂, O₂N) | —NHCOCH₃ | H | —CH₂C≡CH | red |
| 207 | " | " | H | —C₂H₅ | bluish red |
| 208 | 5-phenyl-4-cyanothiazole (H₅C₆, NC, N, S) | H | H | —C₂H₅ | violet |
| 209 | benzothiazole with NCS substituent | H | H | —C₂H₄CN | red |
| 210 | 3-methyl-4-cyano-5-cyanothiophene (H₃C, CN, NC) | —CH₃ | H | —C₂H₅ | violet |

TABLE 3-continued

[Structure: DK—N=N—[benzene ring with R2 (top), R1 (bottom), and N(R3)—CH2CH2—CO—O—CH2—CO—O—CH2CH2N-phthalimide group]]

| exp. no. | DK | R₁ | R₂ | R₃ | Shade on PES |
|---|---|---|---|---|---|
| 211 | [thiophene with H₃C, CN, NC substituents] | —CH₃ | H | —CH₃ | violet |
| 212 | [benzothiazole with O₂N substituent] | —CH₃ | H | " | ruby |
| 213 | " | H | H | C₂H₅ | red |
| 214 | [benzene with two NO₂ and CN substituents] | —NHCOC₂H₅ | H | " | blue |
| 215 | " | —NHCOCH₃ | H | " | " |
| 216 | " | " | H | —C₂H₅/—C₃H₇ (1:1) | " |
| 217 | [benzene with two NO₂ and Br substituents] | " | H | " | bluish violet |
| 218 | [benzene with two NO₂ and Cl substituents] | —NHCOCH₃ | H | —C₂H₅ | bluish violet |
| 219 | H₅C₂O—CO—CH₂—S—[thiadiazole] | " | H | " | red |
| 220 | [phthalide structure] | H | H | —CH₃ | yellow |
| 221 | " | H | H | —C₂H₅ | " |
| 222 | HC≡C—CH₂OC(O)—[phenyl]— | H | H | —CH₃ | " |
| 223 | " | —CH₃ | H | " | " |

TABLE 3-continued
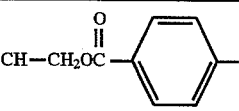
| exp. no. | DK | R₁ | R₂ | R₃ | Shade on PES |
|---|---|---|---|---|---|
| 224 |  | " | H | " | " |
| 225 | " | H | H | " | " |
| 226 | 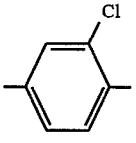 | H | H | " | orange |
| 227 | " | H | H | $-C_2H_5$ | " |
| 228 | " | H | H | $-CH_2CH_2O-CO-OCH_3$ | " |
| 229 | " | $-CH_3$ | H | $-CH_3$ | red |
| 230 | 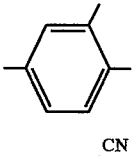 | H | H | " | " |
| 231 | 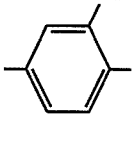 | H | H | $-CH_2CH=CH_2$ | " |
| 232 | 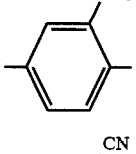 | H | H | $-CH_2CH_2OCOCH_3$ | ruby |
| 233 | " | H | H | $-CH_2CH_2O-CO-OCH_3$ | " |
| 234 | 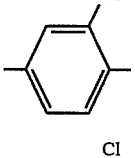 | H | H | $-C_2H_5$ | ruby |
| 235 | 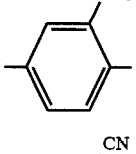 | H | H | $-C_3H_7$ | " |
| 236 | 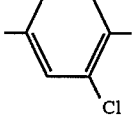 | H | H | " | yellow-brown |
| 237 | " | H | H | $-CH_3$ | " |

The dyestuffs of the following Table 4 correspond to formula
TABLE 4
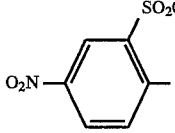
| exp. no. | DK | R₁ | R₂ | R₃ | Shade on PES |
|---|---|---|---|---|---|
| 238 | 4-$O_2N$, 2-$SO_2CH_2CH_3$-phenyl | H | H | —$C_2H_5$ | ruby |
| 239 | 4-$O_2N$, 2-CN-phenyl | H | H | —$CH_3$ | " |
| 240 | " | H | H | —$CH_2CH_2CN$ | red |
| 241 | 4-$O_2N$, 2-$COOCH_3$-phenyl | H | H | —$CH_3$ | " |
| 242 | 4-$O_2N$, 2-Cl-phenyl | H | H | —$C_2H_4CN$ | scarlet |
| 243 | 4-$O_2N$, 2,5-diCl-phenyl | H | H | —$C_2H_4CN$ | scarlet |
| 244 | 4-$O_2N$, 2-Cl-phenyl | —$NHCOCH_3$ | H | " | red |
| 245 | " | " | —Cl | H | scarlet |
| 246 | 4-$O_2N$, 2-CN-phenyl | " | " | H | ruby |
| 247 | 4-$O_2N$, 2-$SO_2CH_3$-phenyl | H | H | —$CH_3$ | " |

TABLE 4-continued
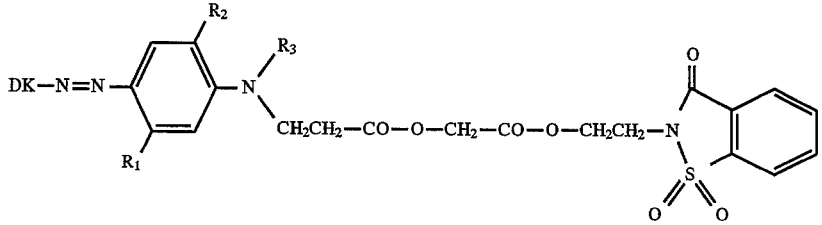
| exp. no. | DK | $R_1$ | $R_2$ | $R_3$ | Shade on PES |
|---|---|---|---|---|---|
| 248 | 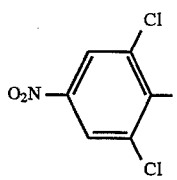 | H | H | —CH$_2$CH=CH$_2$ | yellow-brown |
| 249 | 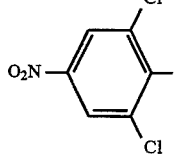 | H | H | —C$_4$H$_9$ | yellow-brown |
| 250 | 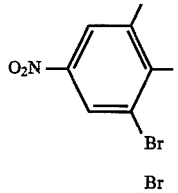 | H | H | —CH$_2$CH=CH$_2$ | " |
| 251 | 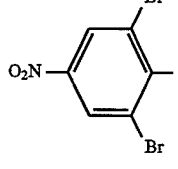 | H | H | " | " |
| 252 | 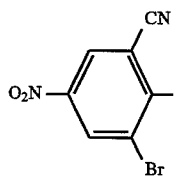 | —NHCOCH$_3$ | H | —C$_2$H$_5$ | bluish violet |
| 253 | 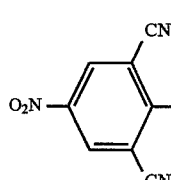 | —CH$_3$ | H | —C$_4$H$_9$ | reddish blue |
| 254 | 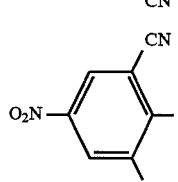 | —NHCOCH$_3$ | H | —C$_3$H$_7$ | blue |
| 255 | " | —NHCOC$_2$H$_5$ | H | " | " |
| 256 | " | —NHCOCH$_3$ | H | —C$_2$H$_5$/—C$_3$H$_7$ (1:1) | " |

TABLE 4-continued

Structure: DK—N=N—[phenyl with R2, R1, N(R3)CH2CH2—CO—O—CH2—CO—O—CH2CH2—N(saccharin)]

| exp. no. | DK | R₁ | R₂ | R₃ | Shade on PES |
|---|---|---|---|---|---|
| 257 | 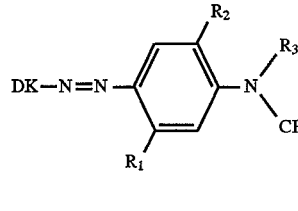 | —CH₃ | H | —C₂H₅ | scarlet |
| 258 | " | —NHCOC₂H₅ | H | " | bluish red |
| 259 | " | —NHSO₂CH₃ | H | C₂H₅/C₃H₇ (1:1) | red |
| 260 | 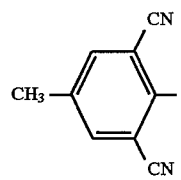 | —NHCOC₂H₅ | H | " | ruby |
| 261 | 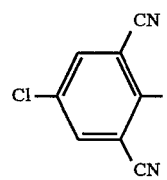 | —CH₃ | H | —C₄H₉ | bluish violet |
| 262 | 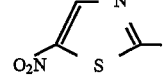 | H | H | —CH₃ | bluish red |
| 263 | " | —CH₃ | H | —C₂H₅ | violet |
| 264 | " | —NHCOCH₃ | H | —C₂H₄CN | bluish red |
| 265 | 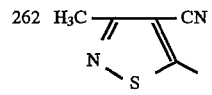 | —CH₃ | H | —C₂H₅ | scarlet |
| 266 | " | —NHCOC₂H₅ | H | " | red |
| 267 | 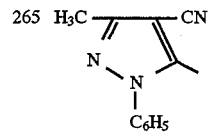 | H | H | —C₂H₅ | scarlet |
| 268 | " | —CH₃ | H | " | red |
| 269 | " | —NHCOCH₃ | H | " | ruby |
| 270 | " | " | H | —C₂H₄CN | red |
| 271 | 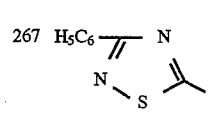 | —CH₃ | H | —C₄H₉ | bluish red |
| 272 | 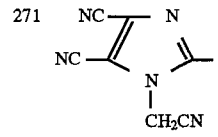 | " | H | —C₂H₅ | dark blue |

TABLE 4-continued

Structure: DK—N=N—[phenyl with R2 (ortho to azo), R1 (meta)]—N(R3)—CH2CH2—CO—O—CH2—CO—O—CH2CH2—N(benzisothiazol-3-one 1,1-dioxide / saccharin-like group)

| exp. no. | DK | R₁ | R₂ | R₃ | Shade on PES |
|---|---|---|---|---|---|
| 273 | " | —NHCOCH₃ | H | —C₂H₅/C₃H₇ (1:1) | greenish blue |
| 274 | 3,5-dinitrothien-2-yl (NO₂ at 3, O₂N at 5) | H | H | —C₂H₅ | blue |
| 275 | " | —CH₃ | H | " | greenish blue |
| 276 | " | H | H | —C₂H₄OCOCH₃ | reddish blue |
| 277 | " | —NHCOCH₃ | H | —C₂H₅ | bluish green |
| 278 | 3-acetyl-5-nitrothien-2-yl (COCH₃, O₂N) | —CH₃ | H | —C₄H₉ | reddish blue |
| 279 | 3-ethoxycarbonyl-5-nitrothien-2-yl (COOC₂H₅, O₂N) | —CH₃ | H | —C₂H₅ | reddish navy blue |
| 280 | 5-(phenylazo)-3-cyanothien-2-yl (H₅C₆—N=N—, CN) | H | H | " | dark blue |
| 281 | 5-(phenylazo)-4-methyl-3-cyanothien-2-yl (H₃C, CN, H₅C₆—N=N—) | H | H | " | " |
| 282 | 5-(4-nitrophenylazo)-3-cyanothien-2-yl (O₂N—C₆H₄—N=N—, CN) | H | H | —C₂H₅ | greenish navy blue |
| 283 | 2,4-dinitrophenyl (NO₂, O₂N) | —NHCOCH₃ | H | —CH₂C≡CH | red |
| 284 | " | " | H | —C₂H₅ | bluish red |
| 285 | 3-phenyl-2-cyanothiazol-5-yl (H₅C₆, NC) | H | H | —C₂H₅ | violet |
| 286 | 6-thiocyanatobenzothiazol-2-yl (NCS) | H | H | —C₂H₄CN | red |
| 287 | 4-methyl-2-cyano-5-cyanothien-... (H₃C, CN, NC) | —CH₃ | H | —C₂H₅ | violet |
| 288 | " | " | H | —CH₃ | violet |

TABLE 4-continued
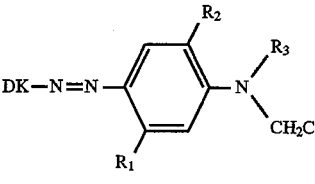
| exp. no. | DK | R₁ | R₂ | R₃ | Shade on PES |
|---|---|---|---|---|---|
| 289 | 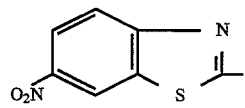 | $-CH_3$ | H | " | ruby |
| 290 | " | H | H | $-C_2H_5$ | red |
| 291 | 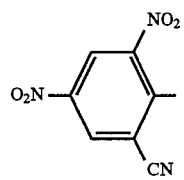 | $-CH_3$ | $-OCH_3$ | $-CH_3$ | blue |
| 292 | " | $-NHCOCH_3$ | H | " | " |
| 293 | " | " | H | $-C_2H_5/-C_3H_7$ (1:1) | " |
| 294 | 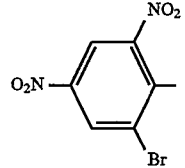 | $-NHCOCH_3$ | H | $-C_2H_5/-C_3H_7$ (1:1) | bluish violet |
| 295 | 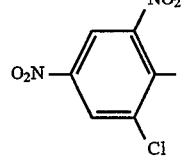 | " | H | $-C_2H_5$ | " |
| 296 | 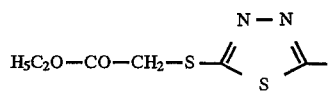 | " | H | " | red |
| 297 | 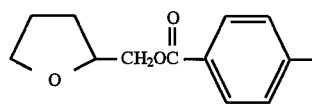 | H | H | $-CH_3$ | yellow |
| 298 | " | H | H | $-C_2H_5$ | " |
| 299 | 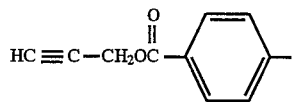 | H | H | $-CH_3$ | " |
| 300 | " | $-CH_3$ | H | " | " |
| 301 | 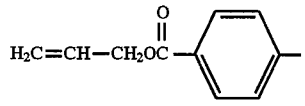 | $-CH_3$ | H | $-CH_3$ | yellow |
| 302 | " | H | H | " | " |

TABLE 4-continued
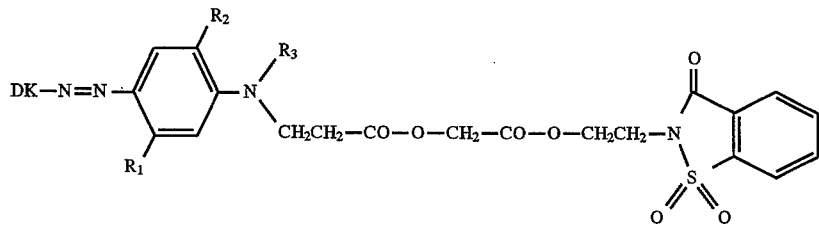
| exp. no. | DK | R₁ | R₂ | R₃ | Shade on PES |
|---|---|---|---|---|---|
| 303 | 4-O₂N-C₆H₄- | H | H | " | orange |
| 304 | " | H | H | —C₂H₅ | " |
| 305 | " | H | H | —CH₂CH₂O—CO—OCH₃ | " |
| 306 | " | —CH₃ | H | —CH₃ | red |
| 307 | 2-Cl-4-O₂N-C₆H₃- | H | H | " | " |
| 308 | 2-Br-4-O₂N-C₆H₃- | H | H | —CH₂CH=CH₂ | " |
| 309 | 2-CN-4-O₂N-C₆H₃- | H | H | —CH₂CH₂OCOCH₃ | ruby |
| 310 | 2-CN-4-O₂N-C₆H₃- | H | H | —CH₂CH₂O—CO—OCH₃ | ruby |
| 311 | 2-SO₂CH₃-4-O₂N-C₆H₃- | H | H | —C₂H₅ | " |
| 312 | 2-CN-4-O₂N-C₆H₃- | H | H | " | " |
| 313 | 2,6-Cl₂-4-O₂N-C₆H₂- | H | H | " | yellow-brown |
| 314 | " | H | H | —CH₃ | " |

TABLE 5

The dyestuffs of the following Table 5 correspond to the formula

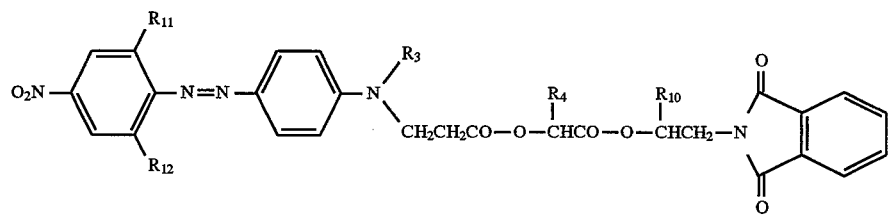

| exp. no. | $R_{11}$ | $R_{12}$ | $R_3$ | $R_4$ | $R_{10}$ | Shade on PES |
|---|---|---|---|---|---|---|
| 315 | Cl | Cl | $-CH_3$ | H | $-CH_3$ | yellow-brown |
| 316 | Cl | Cl | " | $-CH_3$ | H | " |
| 317 | Br | Br | " | H | $-CH_3$ | " |
| 318 | $-CN$ | H | $-CH_2-C_6H_5$ | $-CH_3$ | H | ruby-red |
| 319 | " | H | $-CH_2CH_2-C_6H_5$ | H | $-CH_3$ | " |
| 320 | " | H | $-CH_2CH_2OC_6H_5$ | $-CH_3$ | H | " |
| 321 | " | H | $-CH_2CH_2O-CO-OCH_3$ | H | $-CH_3$ | bluish red |
| 322 | " | H | $-CH_2CH=CH_2$ | H | " | " |
| 323 | Cl | Cl | $-CH_2CH_3$ | H | " | yellow-brown |
| 324 | $-CN$ | H | $-CH_2C\equiv CH$ | $-CH_3$ | H | ruby-red |
| 325 | " | H | $-CH_3$ | H | $-CH_3$ | " |
| 326 | " | H | $-CH_2CH_2OCOOC_2H_5$ | H | " | " |
| 327 | Br | Cl | $-CH_3$ | H | " | yellow-brown |

TABLE 6

The dyestuffs of the following Table 6 correspond to the formula

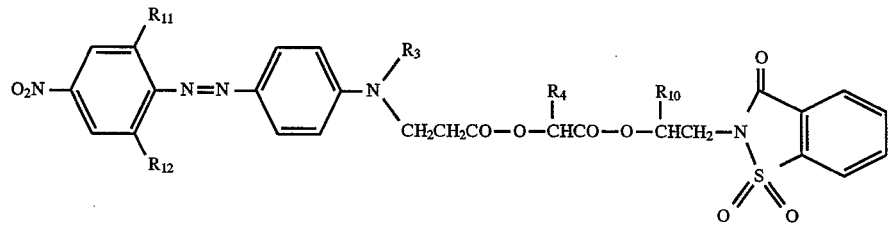

| exp. no. | $R_{11}$ | $R_{12}$ | $R_3$ | $R_4$ | $R_{10}$ | Shade on PES |
|---|---|---|---|---|---|---|
| 328 | Cl | Cl | $-CH_3$ | H | $-CH_3$ | yellow-brown |
| 329 | Cl | Cl | " | $-CH_3$ | H | " |
| 330 | Br | Br | " | H | $-CH_3$ | " |
| 331 | $-CN$ | H | $-CH_2-C_6H_5$ | $-CH_3$ | H | ruby-red |
| 332 | " | H | $-CH_2CH_2-C_6H_5$ | H | $-CH_3$ | " |
| 333 | " | H | $-CH_2CH_2OC_6H_5$ | $-CH_3$ | H | " |
| 334 | " | H | $-CH_2CH_2O-CO-OCH_3$ | H | $-CH_3$ | bluish red |
| 335 | " | H | $-CH_2CH=CH_2$ | H | " | " |
| 336 | Cl | Cl | $-CH_2CH_3$ | H | " | yellow-brown |
| 337 | $-CN$ | H | $-CH_2C\equiv CH$ | $-CH_3$ | H | ruby-red |
| 338 | " | H | $-CH_3$ | H | $-CH_3$ | " |
| 339 | " | H | $-CH_2CH_2OCOOC_2H_5$ | H | " | " |
| 340 | Br | Cl | $-CH_3$ | H | " | yellow-brown |

TABLE 7
The dyestuffs of the following Table 7 correspond to the formula
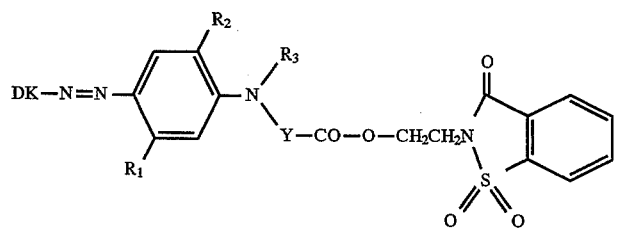
| exp. no. | DK | $R_1$ | $R_2$ | Y | $R_3$ | Shade on PES |
|---|---|---|---|---|---|---|
| 341 | 3-O$_2$N, 2-CN phenyl | H | H | —CH$_2$CH$_2$CH$_2$— | —CH$_3$ | ruby |
| 342 | 3-O$_2$N, 2-SO$_2$CH$_3$ phenyl | H | H | " | " | " |
| 343 | 2-NO$_2$, 4-O$_2$N, 6-Br phenyl | —NHCOCH$_3$ | —OCH$_3$ | " | H | navy blue |
| 344 | 2-NO$_2$, 4-O$_2$N, 6-Cl phenyl | " | —OC$_2$H$_5$ | " | H | " |
| 345 | (CH$_3$)$_2$CH—S-thiadiazolyl | —CH$_3$ | H | —CH$_2$CH$_2$CH$_2$— | —C$_2$H$_5$ | scarlet-red |

TABLE 8 exp. no. 346 — navy blue

[Structure: 2,4-dinitro-6-bromophenyl-azo coupled to quinoline with NH—C₂H₄—COO—CH₂CH₂N(saccharin)]

exp. no. 347 — "

[Structure: 2-chloro-4-nitrophenyl-azo coupled to 8-hydroxynaphthalene with NH—C₂H₄—COO—CH₂CH₂N(saccharin)]

TABLE 9

The dyestuffs of the following Table 9 correspond to the formula

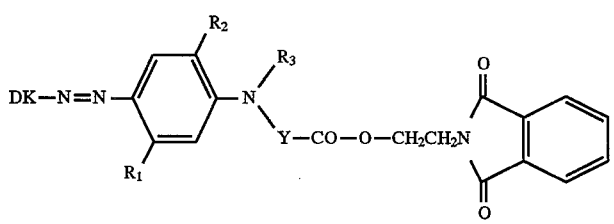

| exp. no. | DK | $R_1$ | $R_2$ | Y | $R_3$ | Shade on PES |
|---|---|---|---|---|---|---|
| 348 | 2-(4-nitrophenyl), 2-CN | H | H | —CH₂CH₂CH₂— | —CH₃ | ruby |
| 349 | 2-(4-nitrophenyl), 2-SO₂CH₃ | H | H | " | " | " |
| 350 | 2,4-dinitro-6-bromophenyl | —NHCOCH₃ | —OCH₃ | " | H | navy blue |
| 351 | 2,4-dinitro-6-chlorophenyl | " | —OC₂H₅ | " | H | " |
| 352 | (CH₃)₂CH—S—(thiadiazolyl) | —CH₃ | H | " | —C₂H₅ | scarlet-red |

TABLE 10

| exp. no. | Structure | Shade |
|---|---|---|
| 353 | 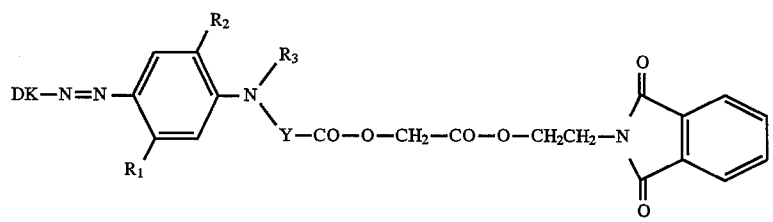 (2,4-dinitro-6-bromophenyl)-N=N-(quinolin-5,8-diyl with NH-C₂H₄-COO-CH₂CH₂N-phthalimide) | navy blue |
| 354 | (2-chloro-4-nitrophenyl)-N=N-(5-hydroxynaphthalen-1,4-diyl with NH-C₂H₄-COO-CH₂CH₂N-phthalimide) | navy blue |

TABLE 11

The dyestuffs of the following Table 11 correspond to formula $$DK-N=N-\underset{R_1}{\underset{|}{\overset{R_2}{\overset{|}{C_6H_2}}}}-N(R_3)-Y-CO-O-CH_2-CO-O-CH_2CH_2-N(phthalimide)$$

| exp. no. | DK | $R_1$ | $R_2$ | Y | $R_3$ | Shade on PES |
|---|---|---|---|---|---|---|
| 355 | 2-CN-4-O₂N-phenyl | H | H | —CH₂CH₂CH₂— | —CH₃ | ruby |
| 356 | 2-CN-4-O₂N-phenyl | H | H | —CH(CH₃)—CH₂— | —CH₃ | ruby |
| 357 | 2-NO₂-4-O₂N-6-Br-phenyl | —NHCOCH₃ | —OCH₃ | —C₃H₆— | H | navy blue |
| 358 | 2-NO₂-4-O₂N-6-Cl-phenyl | " | —OC₂H₅ | " | H | " |
| 359 | (CH₃)₂CH—S—(thiadiazolyl) | —CH₃ | H | " | —C₂H₅ | scarlet-red |

TABLE 12 exp. no. 360: navy blue

Structure: 2,4-dinitro-6-bromophenyl-N=N-naphthyl-NH-C₂H₄-COOCH₂-CO-O-CH₂CH₂-N(phthalimide)

$$\text{O}_2\text{N-C}_6\text{H}_2(\text{NO}_2)(\text{Br})\text{-N=N-(naphthyl)-NH-C}_2\text{H}_4\text{-COOCH}_2\text{-CO-O-CH}_2\text{CH}_2\text{-N(phthalimide)}$$

exp. no. 361: navy blue

Structure: 2-chloro-4-nitrophenyl-N=N-(8-hydroxynaphthyl)-NH-CH(CH₃)-CH₂-COOCH₂-CO-O-CH₂CH₂-N(phthalimide)

TABLE 13

The dyestuffs of Table 13 correspond to formula $$\text{DK-N=N-} \underset{R_1}{\overset{R_2}{\bigcirc}} \text{-N(R}_3\text{)-Y-CO-O-CH}_2\text{-CO-O-CH}_2\text{CH}_2\text{-N(saccharinyl)}$$

| exp. no. | DK | $R_1$ | $R_2$ | Y | $R_3$ | Shade on PES |
|---|---|---|---|---|---|---|
| 362 | 2-CN-4-O₂N-phenyl | H | H | $-CH_2CH_2CH_2-$ | $-CH_3$ | ruby |
| 363 | " | H | H | $-CH(CH_3)-CH_2-$ | " | " |
| 364 | 2-NO₂-4-O₂N-5-Br-phenyl | $-NHCOCH_3$ | $-OCH_3$ | $-C_3H_6-$ | H | navy blue |
| 365 | 2-NO₂-4-O₂N-5-Cl-phenyl | $-NHCOCH_3$ | $-OC_2H_5$ | $-C_3H_6-$ | H | navy blue |
| 366 | (CH₃)₂CH-S-(thiadiazolyl)-N=N- | $-CH_3$ | H | " | $-C_2H_5$ | scarlet-red |

TABLE 14 exp. no. 367: navy blue exp. no. 368: navy blue

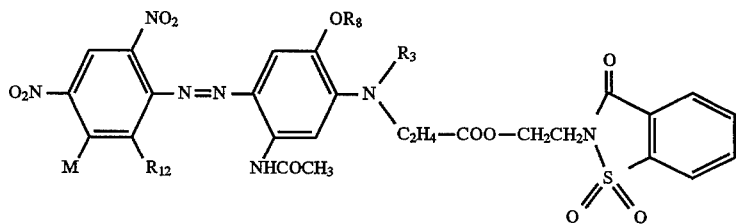

TABLE 15

The dyestuffs of following Table 15 correspond to formula

| exp. no. | M | $R_{12}$ | $R_8$ | $R_3$ | Shade on PES |
|---|---|---|---|---|---|
| 369 | H | —Br | —$CH_3$ | H | navy blue |
| 370 | H | " | —$C_2H_5$ | H | " |
| 371 | H | " | —$C_2H_4OCH_3$ | H | " |
| 372 | —Cl | —Cl | " | H | " |
| 373 | H | " | —$C_2H_4OCH_3$ | H | " |
| 374 | H | " | —$C_2H_5$ | H | " |
| 375 | H | " | —$CH_3$ | —$C_2H_5$ | greenish navy blue |
| 376 | H | " | " | —$CH_2$—CH=$CH_2$ | navy blue |
| 377 | H | —Br | " | —$CH_2$—CH=CHCl | reddish navy blue |
| 378 | H | —Cl | " | —$CH_2$—C≡CH | " |
| 379 | H | " | " | —$CH_2$—$C_6H_5$ | navy blue |
| 380 | H | " | —$C_2H_5$ | —$CH_2$—CH=$CH_2$ | " |
| 381 | H | " | " | —$CH_2$CH=CH—Cl | " |
| 382 | H | " | " | —$CH_3$—C≡CH | reddish navy blue |
| 383 | H | —Cl | —$CH_3$ | —$C_2H_4$—$C_6H_5$ | greenish navy blue |
| 384 | H | " | " | —$C_3H_6O$—$C_6H_5$ | " |
| 385 | H | H | " | —CH—CH=CH—Cl | reddish navy blue |
| 386 | H | -J | " | —$CH_2$—CH=$CH_2$ | " |
| 387 | H | —CN | " | " | greenish blue |
| 388 | H | " | " | —$C_2H_5$ | bluish green |

TABLE 16

The dyestuffs of following Table 16 correspond to formula

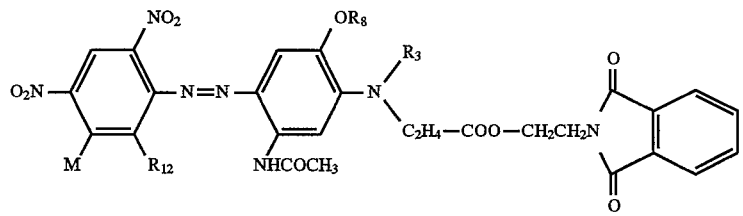

| exp. no. | M | $R_{12}$ | $R_8$ | $R_3$ | Shade on PES |
|---|---|---|---|---|---|
| 389 | H | —Br | —CH$_3$ | H | navy blue |
| 390 | H | " | —C$_2$H$_5$ | H | " |
| 391 | H | " | —C$_2$H$_4$OCH$_3$ | H | " |
| 392 | H | —Cl | —CH$_3$ | H | " |
| 393 | —Cl | —Cl | " | H | " |
| 394 | H | " | —C$_2$H$_4$OCH$_3$ | H | " |
| 395 | H | " | —C$_2$H$_5$ | H | " |
| 396 | H | " | —CH$_3$ | —C$_2$H$_5$ | greenish navy blue |
| 397 | H | " | " | —CH$_2$—CH=CH$_2$ | navy blue |
| 398 | H | —Br | " | —CH$_2$—CH=CHCl | reddish navy blue |
| 399 | H | —Cl | " | —CH$_2$—C≡CH | " |
| 400 | H | " | " | —CH$_2$—C$_6$H$_5$ | navy blue |
| 401 | H | " | —C$_2$H$_5$ | —CH$_2$CH=CH$_2$ | " |
| 402 | H | " | " | —CH$_2$—CH=CH—Cl | " |
| 403 | H | " | " | —CH$_3$—C≡CH | reddish navy blue |
| 404 | H | —Cl | —CH$_3$ | —C$_2$H$_4$—C$_6$H$_5$ | greenish navy blue |
| 405 | H | " | " | —C$_3$H$_6$O—C$_6$H$_5$ | " |
| 406 | H | H | " | —CH—CH=CH—Cl | reddish navy blue |
| 407 | H | -J | " | —CH$_2$—CH=CH$_2$ | " |
| 408 | H | —CN | " | " | greenish blue |
| 409 | H | " | " | —C$_2$H$_5$ | bluish green |

TABLE 17

The dyestuffs of following Table 17 correspond to formula

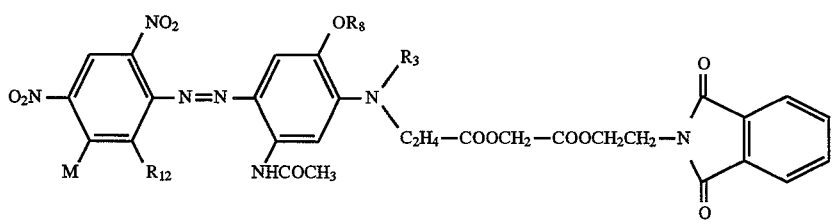

| exp. no. | M | $R_{12}$ | $R_8$ | $R_3$ | Shade on PES |
|---|---|---|---|---|---|
| 410 | H | —Br | —CH$_3$ | H | navy blue |
| 411 | H | " | —C$_2$H$_5$ | H | " |
| 412 | H | " | —C$_2$H$_4$OCH$_3$ | H | " |
| 413 | H | —Cl | —CH$_3$ | H | " |
| 414 | —Cl | —Cl | " | H | " |
| 415 | H | " | —C$_2$H$_4$OCH$_3$ | H | " |
| 416 | H | " | —C$_2$H$_5$ | H | " |
| 417 | H | " | —CH$_3$ | —C$_2$H$_5$ | greenish navy blue |
| 418 | H | " | " | —CH$_2$—CH=CH$_2$ | navy blue |
| 419 | H | —Br | " | —CH$_2$—CH=CHCl | reddish navy blue |

TABLE 17-continued

The dyestuffs of following Table 17 correspond to formula

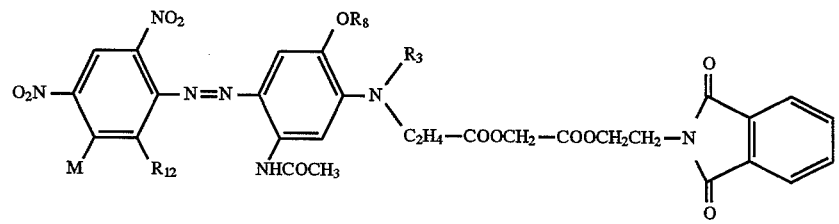

| exp. no. | M | $R_{12}$ | $R_8$ | $R_3$ | Shade on PES |
|---|---|---|---|---|---|
| 420 | H | —Cl | " | —$CH_2$—C≡CH | " |
| 421 | H | " | " | —$CH_2$—$C_6H_5$ | navy blue |
| 422 | H | " | —$C_2H_5$ | —$CH_2$—CH=$CH_2$ | " |
| 423 | H | " | " | —$CH_2$—CH=CH—Cl | " |
| 424 | H | " | " | —$CH_3$—C≡CH | reddish navy blue |
| 425 | H | —Cl | —$CH_3$ | —$C_2H_4$—$C_6H_5$ | greenish navy blue |
| 426 | H | " | " | —$C_3H_6O$—$C_6H_5$ | " |
| 427 | H | H | " | —CH—CH=CH—Cl | reddish navy blue |
| 428 | H | -J | " | —$CH_2$—CH=$CH_2$ | " |
| 429 | H | —CN | " | " | greenish blue |
| 430 | H | " | " | —$C_2H_5$ | bluish green |

30

TABLE 18

The dyestuffs of following Table 18 correspond to formula

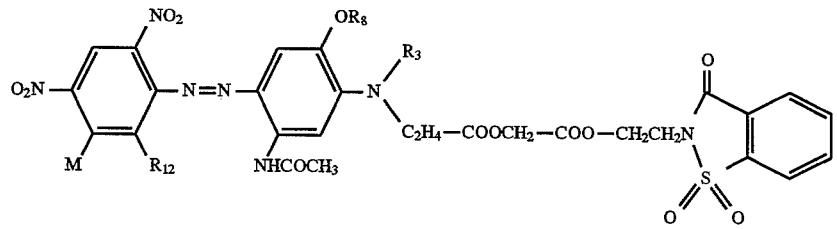

| exp. no. | M | $R_{12}$ | $R_8$ | $R_3$ | Shade on PES |
|---|---|---|---|---|---|
| 431 | H | —Br | —$CH_3$ | H | navy blue |
| 432 | H | " | —$C_2H_5$ | H | " |
| 433 | H | " | —$C_2H_4OCH_3$ | H | " |
| 434 | H | —Cl | —$CH_3$ | H | " |
| 435 | —Cl | —Cl | " | H | " |
| 436 | H | " | —$C_2H_4OCH_3$ | H | " |
| 437 | H | " | —$C_2H_5$ | H | " |
| 438 | H | " | —$CH_3$ | —$C_2H_5$ | greenish navy blue |
| 439 | H | " | " | —$CH_2$—CH=$CH_2$ | navy blue |
| 440 | H | —Br | " | —$CH_2$—CH=CHCl | reddish navy blue |
| 441 | H | —Cl | " | —$CH_2$—C≡CH | " |
| 442 | H | " | " | —$CH_2$—$C_6H_5$ | navy blue |
| 443 | H | " | —$C_2H_5$ | —$CH_2$—CH=$CH_2$ | " |
| 444 | H | " | " | —$CH_2$—CH=CH—Cl | " |
| 445 | H | " | " | —$CH_3$—C≡CH | reddish navy blue |
| 446 | H | —Cl | —$CH_3$ | —$C_2H_4$—$C_6H_5$ | greenish navy blue |
| 447 | H | " | " | —$C_3H_6O$—$C_6H_5$ | " |

TABLE 18-continued

The dyestuffs of following Table 18 correspond to formula

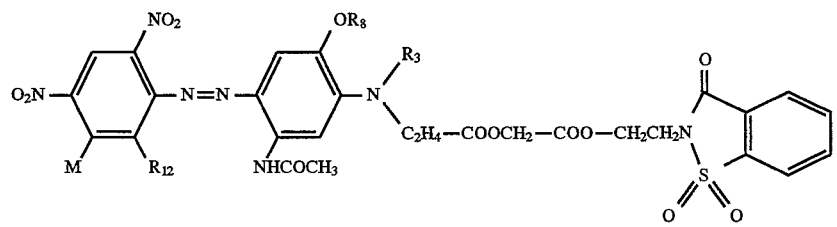

| exp. no. | M | $R_{12}$ | $R_8$ | $R_3$ | Shade on PES |
|---|---|---|---|---|---|
| 448 | H | H | " | —CH—CH=CH—Cl | reddish navy blue |
| 449 | H | -J | " | —CH$_2$—CH=CH$_2$ | " |
| 450 | H | —CN | " | " | greenish blue |
| 451 | H | " | " | —C$_2$H$_5$ | bluish green |

TABLE 19

The dyestuffs of the following Table 19 correspond to formula

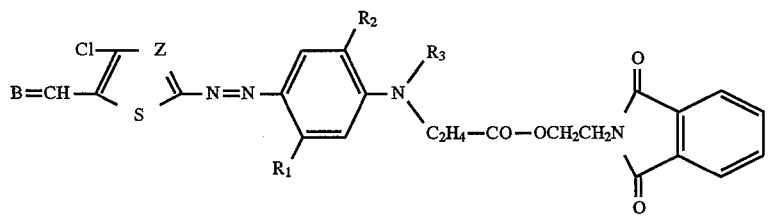

| exp. no. | B | Z | $R_1$ | $R_2$ | $R_3$ | Shade on PES |
|---|---|---|---|---|---|---|
| 452 | =O | $=C-CN$ | —CH$_3$ | H | —C$_2$H$_5$ | blue |
| 453 | =O | " | " | H | —C$_4$H$_9$ | " |
| 454 | =CH—NO$_2$ | " | " | H | —C$_2$H$_5$ | greenish blue |
| 455 | =C(CN)(COOC$_2$H$_5$/C$_4$H$_9$(1:1)) | " | " | H | " | " |
| 456 | =O | " | —NHCOCH$_3$ | H | " | reddish blue |
| 457 | =O | =N— | —CH$_3$ | H | " | violet |
| 458 | =O | " | —NHCOCH$_3$ | —OCH$_3$ | H | navy blue |
| 459 | =O | " | " | " | —CH$_2$—CH=CH$_2$ | " |
| 460 | =O | " | " | " | —CH$_2$—HC=CH—Cl | " |
| 461 | =O | " | " | —OC$_2$H$_5$ | " | " |
| 462 | =O | " | " | " | —CH$_2$CH=CH$_2$ | " |
| 463 | =O | " | " | —OC$_2$H$_4$OCH$_3$ | " | " |
| 464 | =O | " | " | —OC$_2$H$_5$ | H | " |
| 465 | O$_2$N—CH= | " | —CH$_3$ | H | —C$_2$H$_5$ | blue |
| 466 | NC\C=/COOC$_4$H$_9$ | " | " | —OCH$_3$ | " | " |

TABLE 20

The dyestuffs of the following Table 20 correspond to formula

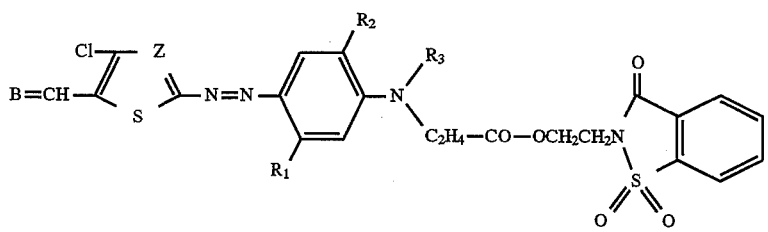

| exp. no. | B | Z | R₁ | R₂ | R₃ | Shade on PES |
|---|---|---|---|---|---|---|
| 467 | =O | $\underset{=C-CN}{\|}$ | $-CH_3$ | H | $-C_2H_5$ | blue |
| 468 | =O | " | " | H | $-C_4H_9$ | " |
| 469 | $=CH-NO_2$ | " | " | H | $-C_2H_5$ | greenish blue |
| 470 | $=C\begin{smallmatrix}CN\\COOC_2H_5/\\C_4H_9(1:1)\end{smallmatrix}$ | " | " | H | " | " |
| 471 | =O | " | $-NHCOCH_3$ | H | " | reddish blue |
| 472 | =O | =N— | $-CH_3$ | H | " | violet |
| 473 | =O | " | $-NHCOCH_3$ | $-OCH_3$ | H | navy blue |
| 474 | =O | " | " | " | $-CH_2-CH=CH_2$ | " |
| 475 | =O | " | " | " | $-CH_2-HC=CH-Cl$ | " |
| 476 | =O | " | " | $-OC_2H_5$ | " | " |
| 477 | =O | " | " | " | $-CH_2CH=CH_2$ | " |
| 478 | =O | " | " | $-OC_2H_4OCH_3$ | " | " |
| 479 | =O | " | " | $-OC_2H_5$ | H | " |
| 480 | $O_2N-CH=$ | " | $-CH_3$ | H | $-C_2H_5$ | blue |
| 481 | $\begin{smallmatrix}NC\\\\COOC_4H_9\end{smallmatrix}C=$ | " | " | $-OCH_3$ | " | " |

TABLE 21

The dyestuffs of the following Table 21 correspond to formula

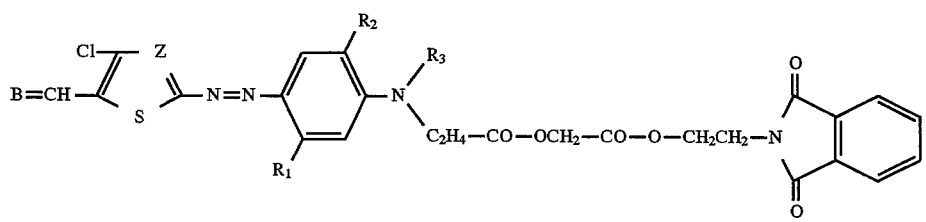

| exp. no. | B | Z | R₁ | R₂ | R₃ | Shade on PES |
|---|---|---|---|---|---|---|
| 482 | =O | $\underset{=C-CN}{\|}$ | $-CH_3$ | H | $-C_2H_5$ | blue |
| 483 | =O | " | " | H | $-C_4H_9$ | " |
| 484 | $=CH-NO_2$ | " | " | H | $-C_2H_5$ | greenish blue |

TABLE 21-continued

The dyestuffs of the following Table 21 correspond to formula

| exp. no. | B | Z | $R_1$ | $R_2$ | $R_3$ | Shade on PES |
|---|---|---|---|---|---|---|
| 485 | =C(CN)(COOC$_2$H$_5$/C$_4$H$_9$(1:1)) | " | " | H | " | " |
| 486 | =O | " | —NHCOCH$_3$ | H | " | reddish blue |
| 487 | =O | =N— | —CH$_3$ | H | " | violet |
| 488 | =O | " | —NHCOCH$_3$ | —OCH$_3$ | H | navy blue |
| 489 | =O | " | " | " | —CH$_2$—CH=CH$_2$ | " |
| 490 | =O | " | " | " | —CH$_2$—HC=CH—Cl | " |
| 491 | =O | " | " | —OC$_2$H$_5$ | " | " |
| 492 | =O | " | " | " | —CH$_2$CH=CH$_2$ | " |
| 493 | =O | " | " | —OC$_2$H$_4$OCH$_3$ | " | " |
| 494 | =O | " | " | —OC$_2$H$_5$ | H | " |
| 495 | O$_2$N—CH= | " | —CH$_3$ | H | —C$_2$H$_5$ | blue |
| 497 | =C(NC)(COOC$_4$H$_9$) | " | " | —OCH$_3$ | " | " |

TABLE 22

The dyestuffs of the following Table 22 correspond to formula

| exp. no. | B | Z | $R_1$ | $R_2$ | $R_3$ | Shade on PES |
|---|---|---|---|---|---|---|
| 498 | =O | =C(—CN)— | —CH$_3$ | H | —C$_2$H$_5$ | blue |
| 499 | =O | " | " | H | —C$_4$H$_9$ | " |
| 500 | =CH—NO$_2$ | " | " | H | —C$_2$H$_5$ | greenish blue |
| 501 | =C(CN)(COOC$_2$H$_5$/C$_4$H$_9$(1:1)) | " | " | H | " | " |
| 502 | =O | " | —NHCOCH$_3$ | H | " | reddish blue |
| 503 | =O | =N— | —CH$_3$ | H | " | violet |
| 504 | =O | " | —NHCOCH$_3$ | —OCH$_3$ | H | navy blue |

TABLE 22-continued

The dyestuffs of the following Table 22 correspond to formula

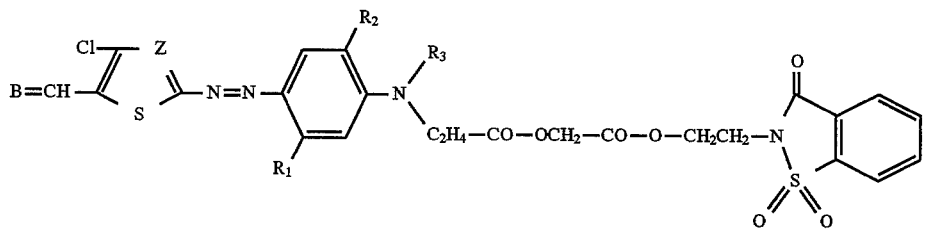

| exp. no. | B | Z | $R_1$ | $R_2$ | $R_3$ | Shade on PES |
|---|---|---|---|---|---|---|
| 505 | =O | " | " | " | $-CH_2-CH=CH_2$ | " |
| 506 | =O | " | " | " | $-CH_2-HC=CH-Cl$ | " |
| 507 | =O | " | " | $-OC_2H_5$ | " | " |
| 508 | =O | " | " | " | $-CH_2CH=CH_2$ | " |
| 509 | =O | " | " | $-OC_2H_4OCH_3$ | " | " |
| 510 | =O | " | " | $-OC_2H_5$ | H | " |
| 511 | $O_2N-CH=$ | " | $-CH_3$ | H | $-C_2H_5$ | blue |
| 512 | $NC\!\!\diagdown\!\!\!\!\!\!\!\!\!\underset{COOC_4H_9}{C=}$ | " | " | $-OCH_3$ | " | " |

TABLE 23

The dyestuffs of the following Table 23 correspond to formula

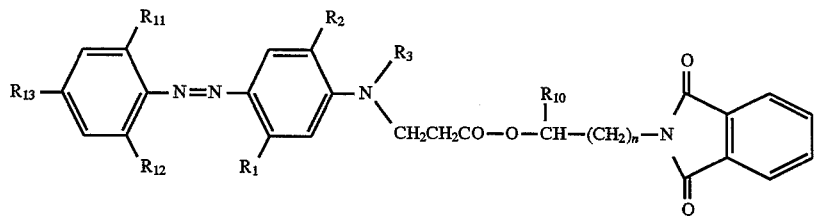

| exp. no. | $R_{11}$ | $R_{12}$ | $R_{13}$ | $R_1$ | $R_2$ | $R_3$ | $R_{10}$ | Shade on PES |
|---|---|---|---|---|---|---|---|---|
| 513 | $-CN$ | H | $-NO_2$ | H | H | $-CH_3$ | $-CH_3$ | 1 ruby |
| 514 | " | H | " | H | H | " | H | 2 ruby |
| 515 | " | H | " | H | H | " | H | 3 ruby |
| 516 | " | H | " | H | H | " | H | 4 ruby |
| 517 | " | H | " | H | H | " | H | 5 ruby |
| 518 | Cl | Cl | " | H | H | " | $-CH_3$ | 1 yellow-brown |
| 519 | Cl | Cl | " | H | H | " | H | 2 yellow-brown |
| 520 | $-NO_2$ | Cl | " | $-NHCOCH_3$ | $-OCH_3$ | H | $-CH_3$ | 1 navy blue |
| 521 | " | Cl | " | " | " | H | H | 2 navy blue |
| 522 | " | Cl | " | " | " | $-CH_2CH=CH_2$ | H | 2 navy blue |
| 523 | " | $-CN$ | " | $-CH_3$ | " | $-CH_3$ | H | 2 blue |
| 524 | " | $-CN$ | " | " | H | " | H | 2 reddish blue |

TABLE 24

The dyestuffs of the following Table 25 correspond to formula

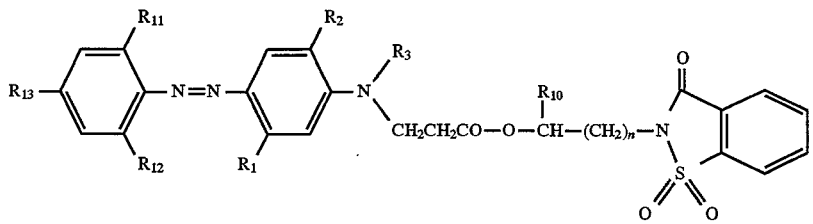

| exp. no. | $R_{11}$ | $R_{12}$ | $R_{13}$ | $R_1$ | $R_2$ | $R_3$ | $R_{10}$ | n | Shade on PES |
|---|---|---|---|---|---|---|---|---|---|
| 525 | —CN | H | —$NO_2$ | H | H | —$CH_3$ | —$CH_3$ | 1 | ruby |
| 526 | " | H | " | H | H | " | H | 2 | " |
| 527 | Cl | Cl | " | H | H | " | H | 2 | yellow-brown |
| 528 | —$NO_2$ | Cl | " | —$NHCOCH_3$ | —$OCH_3$ | H | H | 2 | navy blue |
| 529 | " | Br | " | " | " | H | —$CH_3$ | 1 | " |
| 530 | " | CN | " | —$CH_3$ | " | —$CH_3$ | H | 2 | blue |
| 531 | " | " | " | " | H | —$C_2H_5$ | H | 2 | reddish blue |
| 532 | " | " | " | —$CH_3$ | —$OCH_3$ | —$CH_3$ | H | 1 | blue |
| 533 | " | " | " | —$CH_3$ | " | —$C_2H_5$ | H | 1 | " |
| 534 | Cl | H | —$NO_2$ | H | H | —$CH_2CH_2OCOCH_3$ | H | 2 | scarlet |
| 535 | —CN | —CN | " | —$CH_3$ | H | —$C_2H_5$ | H | 2 | blue |

TABLE 25

The dyestuffs of following Table 25 correspond to formula

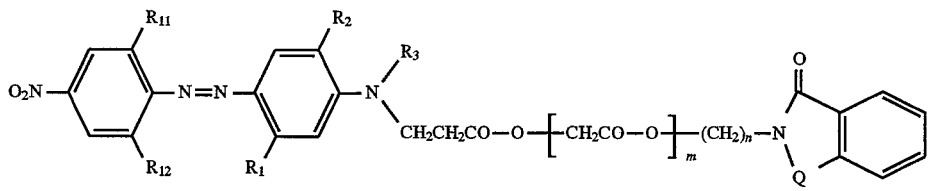

| exp. no. | $R_{11}$ | $R_{12}$ | $R_1$ | $R_2$ | $R_3$ | m | n | Q | Shade on PES |
|---|---|---|---|---|---|---|---|---|---|
| 536 | —$NO_2$ | —CN | —$CH_3$ | $OCH_3$ | $CH_3$ | 1 | 3 | \C/ ‖ O | blue |
| 537 | " | " | " | H | " | 1 | 3 | " | reddish blue |
| 538 | " | Br | " | H | $C_2H_5$ | 1 | 3 | " | violet |
| 539 | " | Cl | —$NHCOCH_3$ | $OCH_3$ | —$CH_2CH=CH_2$ | 0 | 3 | " | navy blue |
| 540 | —CN | H | H | H | —$CH_3$ | 1 | 3 | " | ruby |
| 541 | —Cl | Cl | H | H | " | 1 | 3 | " | yellow-brown |
| 542 | —$NO_2$ | —CN | —$CH_3$ | H | " | 0 | 2 | " | reddish blue |
| 543 | " | " | " | H | —$C_2H_5$ | 0 | 2 | " | " |
| 544 | " | " | " | —$OCH_3$ | —$CH_3$ | 0 | 3 | \S/ ∥ ∥ O O | blue |
| 545 | " | " | " | H | —$C_2H_5$ | 1 | 3 | " | reddish blue |
| 546 | " | " | " | H | —$CH_3$ | 1 | 3 | " | " |
| 547 | CN | H | H | H | " | 1 | 3 | " | ruby |
| 548 | $NO_2$ | Cl | —$NHCOCH_3$ | —$OCH_3$ | H | 1 | 3 | " | navy blue |

APPLICATION EXAMPLE

The dyestuff obtained according to example 1 is converted by means of sand-grinding in the presence of dispersing agents, e.g. commercial lignin sulphonate, with subsequent fine disintegration, into an ultra-disperse dye preparation having an average particle size of 1 μm and a dilution ratio of 3.5:10.

12 parts of this preparation are made into a dispersion with 1000 parts of water, and added to the circulating liquor (13,000 parts, containing 30 parts of ammonium sulphate and 0.3 parts of formic acid as a buffer and optionally a carrier/levelling agent combination) at 60°. The pre-cleaned, compressed, cross-wound spool (1000 parts of polyester yarn on a plastic sleeve) is introduced, the dyeing autoclave closed, and heated in 35 minutes to 130°. After 90 minutes, cooling is effected to 80°, the exhausted liquor is drained, and the substrate thus dyed is washed thoroughly with cold water, and purified by reduction in the usual manner. It is then centrifuged and dried. A level, pure, deep ruby-red dyeing is obtained.

Dyeing of polyester yarn can be carried out analogously with examples 2–548, whereby yielding a level, deep dyeing.

The following table gives the $\lambda_{max}$-values of the above examples measured in dimethylformamide (DMF).

| exp. no. | $\lambda_{max}$ nm | exp. no. | $\lambda_{max}$ nm |
|---|---|---|---|
| 8 | 532 | 26 | 614 |
| 9 | 527 | 27 | 511 |
| 10 | 508 | 28 | 530 |
| 11 | 494 | 29 | 517 |
| 12 | 490 | 30 | 542 |
| 13 | 489 | 31 | 600 |
| 14 | 520 | 32 | 541 |
| 15 | 510 | 33 | 545 |
| 16 | 530 | 35 | 517 |
| 17 | 527 | 36 | 537 |
| 18 | 435 | 37 | 524 |
| 19 | 443 | 38 | 534 |
| 20 | 433 | 39 | 544 |
| 21 | 432 | 42 | 604 |
| 22 | 583 | 44 | 645 |
| 23 | 604 | 45 | 660 |
| 24 | 615 | 46 | 630 |
| 25 | 616 | 48 | 625 |
| 49 | 622 | 70 | 456 |
| 50 | 625 | 71 | 459 |
| 51 | 626 | 72 | 446 |
| 52 | 661 | 73 | 487 |
| 53 | 529 | 74 | 492 |
| 54 | 550 | 75 | 488 |
| 55 | 556 | 76 | 497 |
| 56 | 510 | 77 | 509 |
| 57 | 587 | 78 | 502 |
| 58 | 584 | 79 | 526 |
| 59 | 558 | 80 | 524 |
| 60 | 549 | 81 | 532 |
| 61 | 605 | 82 | 536 |
| 62 | 605 | 83 | 443 |
| 63 | 606 | 84 | 532 |
| 64 | 572 | 85 | 538 |
| 65 | 561 | 86 | 515 |
| 66 | 525 | 87 | 495 |
| 67 | 451 | 88 | 490 |
| 68 | 457 | 89 | 489 |
| 69 | 449 | 90 | 521 |
| 91 | 511 | 113 | 525 |
| 92 | 531 | 114 | 534 |
| 93 | 532 | 115 | 544 |
| 94 | 435 | 118 | 605 |
| 95 | 443 | 120 | 646 |
| 96 | 433 | 121 | 661 |
| 97 | 432 | 122 | 631 |
| 98 | 584 | 124 | 625 |
| 99 | 605 | 125 | 622 |
| 100 | 616 | 126 | 626 |
| 101 | 617 | 127 | 626 |
| 102 | 615 | 128 | 661 |
| 103 | 512 | 129 | 530 |
| 104 | 531 | 130 | 551 |
| 105 | 518 | 131 | 557 |
| 106 | 543 | 132 | 511 |
| 107 | 601 | 133 | 588 |
| 108 | 542 | 134 | 585 |
| 109 | 545 | 135 | 559 |
| 111 | 518 | 136 | 550 |
| 112 | 538 | 137 | 606 |
| 138 | 606 | 159 | 443 |
| 139 | 607 | 160 | 440 |
| 140 | 560 | 161 | 527 |
| 141 | 562 | 162 | 539 |
| 142 | 526 | 163 | 513 |
| 143 | 452 | 164 | 493 |
| 144 | 458 | 165 | 489 |
| 145 | 449 | 166 | 488 |
| 146 | 456 | 167 | 519 |
| 147 | 459 | 168 | 509 |
| 148 | 446 | 169 | 529 |
| 149 | 487 | 170 | 526 |
| 150 | 492 | 171 | 435 |
| 151 | 489 | 172 | 443 |
| 152 | 498 | 173 | 433 |
| 153 | 509 | 174 | 432 |
| 154 | 503 | 175 | 582 |
| 155 | 527 | 176 | 603 |
| 156 | 525 | 177 | 614 |
| 157 | 527 | 178 | 615 |
| 158 | 538 | 179 | 613 |
| 180 | 510 | 206 | 528 |
| 181 | 529 | 207 | 549 |
| 182 | 516 | 208 | 555 |
| 183 | 514 | 209 | 509 |
| 184 | 599 | 210 | 586 |
| 185 | 540 | 211 | 583 |
| 186 | 544 | 212 | 557 |
| 188 | 516 | 213 | 548 |
| 189 | 536 | 214 | 604 |
| 190 | 523 | 215 | 604 |
| 191 | 533 | 216 | 605 |
| 192 | 543 | 217 | 558 |
| 195 | 603 | 218 | 560 |
| 197 | 644 | 219 | 524 |
| 198 | 659 | 220 | 450 |
| 199 | 629 | 221 | 456 |
| 201 | 624 | 222 | 448 |
| 202 | 621 | 223 | 455 |
| 203 | 624 | 224 | 458 |
| 204 | 624 | 225 | 445 |
| 205 | 660 | 226 | 486 |
| 227 | 491 | 248 | 435 |
| 228 | 487 | 249 | 441 |
| 229 | 496 | 250 | 432 |
| 230 | 508 | 251 | 431 |
| 231 | 501 | 252 | 582 |
| 232 | 525 | 253 | 603 |
| 233 | 523 | 254 | 614 |
| 234 | 531 | 255 | 615 |
| 235 | 540 | 256 | 613 |
| 236 | 442 | 257 | 510 |
| 237 | 439 | 258 | 529 |
| 238 | 530 | 259 | 516 |
| 239 | 532 | 260 | 542 |
| 240 | 513 | 261 | 599 |
| 241 | 493 | 262 | 540 |
| 242 | 487 | 263 | 544 |
| 243 | 487 | 265 | 516 |
| 244 | 519 | 266 | 536 |
| 245 | 509 | 267 | 523 |
| 246 | 529 | 268 | 533 |
| 247 | 527 | 269 | 544 |
| 272 | 603 | 295 | 560 |
| 274 | 644 | 296 | 524 |
| 275 | 659 | 297 | 445 |
| 276 | 629 | 298 | 451 |
| 278 | 624 | 299 | 448 |
| 279 | 621 | 300 | 455 |
| 280 | 624 | 301 | 458 |
| 281 | 625 | 302 | 445 |
| 282 | 660 | 303 | 486 |
| 283 | 528 | 304 | 491 |
| 284 | 549 | 305 | 487 |
| 285 | 555 | 306 | 496 |

| exp. no. | λ_max nm | exp. no. | λ_max nm | exp. no. | λ_max nm | exp. no. | λ_max nm |
|---|---|---|---|---|---|---|---|
| 286 | 509 | 307 | 508 | 467 | 612 | 493 | 624 |
| 287 | 586 | 308 | 502 | 468 | 613 | 494 | 609 |
| 288 | 583 | 309 | 525 | 470 | 639 | 497 | 679 |
| 289 | 557 | 310 | 523 | 472 | 587 | 498 | 610 |
| 290 | 548 | 311 | 530 | 473 | 611 | 499 | 612 |
| 291 | 604 | 312 | 536 | 474 | 624 | 501 | 637 |
| 292 | 604 | 313 | 442 | 475 | 613 | 503 | 586 |
| 293 | 605 | 314 | 439 | 476 | 615 | 504 | 609 |
| 294 | 558 | 315 | 440 | 477 | 627 | 505 | 623 |
| 316 | 441 | 337 | 516 | 478 | 626 | 506 | 612 |
| 317 | 437 | 338 | 533 | 479 | 611 | 507 | 614 |
| 318 | 530 | 339 | 524 | 481 | 681 | 508 | 625 |
| 319 | 534 | 340 | 439 | 482 | 610 | 509 | 624 |
| 320 | 530 | 341 | 542 | 483 | 612 | 510 | 609 |
| 321 | 524 | 342 | 537 | 485 | 637 | 512 | 679 |
| 322 | 530 | 343 | 607 | 513 | 534 | 531 | 601 |
| 323 | 443 | 344 | 610 | 514 | 535 | 532 | 614 |
| 324 | 516 | 346 | 583 | 515 | 535 | 533 | 619 |
| 325 | 533 | 347 | 622 | 516 | 536 | 534 | 511 |
| 326 | 524 | 348 | 543 | 517 | 536 | 535 | 619 |
| 327 | 439 | 349 | 537 | 518 | 440 | 536 | 613 |
| 328 | 440 | 350 | 607 | 519 | 440 | 537 | 588 |
| 329 | 441 | 351 | 609 | 520 | 597 | 538 | 557 |
| 330 | 530 | 354 | 621 | 521 | 597 | 539 | 599 |
| 331 | 530 | 354 | 621 | 522 | 599 | 540 | 533 |
| 332 | 534 | 355 | 541 | 523 | 613 | 541 | 439 |
| 333 | 530 | 356 | 540 | 524 | 587 | 542 | 587 |
| 334 | 524 | 357 | 605 | 525 | 535 | 543 | 593 |
| 335 | 530 | 358 | 607 | 526 | 536 | 544 | 613 |
| 336 | 443 | 360 | 602 | 527 | 441 | 545 | 590 |
| 361 | 628 | 386 | 599 | 528 | 598 | 546 | 587 |
| 362 | 541 | 387 | 634 | 529 | 598 | 547 | 534 |
| 363 | 539 | 388 | 637 | 530 | 595 | 548 | 598 |
| 364 | 605 | 389 | 597 | | | | |
| 365 | 607 | 390 | 597 | | | | |
| 367 | 602 | 391 | 594 | | | | |
| 368 | 629 | 392 | 598 | | | | |
| 369 | 597 | 393 | 585 | | | | |
| 370 | 597 | 394 | 593 | | | | |
| 371 | 594 | 395 | 599 | | | | |
| 372 | 581 | 396 | 603 | | | | |
| 373 | 593 | 397 | 599 | | | | |
| 374 | 600 | 398 | 589 | | | | |
| 375 | 604 | 399 | 574 | | | | |
| 376 | 599 | 401 | 600 | | | | |
| 377 | 589 | 402 | 591 | | | | |
| 378 | 573 | 403 | 575 | | | | |
| 380 | 601 | 406 | 564 | | | | |
| 381 | 592 | 407 | 598 | | | | |
| 382 | 576 | 408 | 633 | | | | |
| 385 | 565 | 409 | 635 | | | | |
| 410 | 596 | 434 | 596 | | | | |
| 411 | 596 | 435 | 583 | | | | |
| 412 | 593 | 436 | 592 | | | | |
| 413 | 597 | 437 | 598 | | | | |
| 414 | 584 | 438 | 602 | | | | |
| 415 | 592 | 439 | 598 | | | | |
| 416 | 598 | 440 | 588 | | | | |
| 417 | 602 | 441 | 571 | | | | |
| 418 | 598 | 443 | 600 | | | | |
| 419 | 588 | 444 | 590 | | | | |
| 420 | 574 | 445 | 574 | | | | |
| 422 | 598 | 448 | 564 | | | | |
| 423 | 590 | 449 | 598 | | | | |
| 424 | 574 | 450 | 633 | | | | |
| 427 | 563 | 451 | 636 | | | | |
| 428 | 596 | 452 | 611 | | | | |
| 429 | 632 | 453 | 613 | | | | |
| 430 | 635 | 455 | 638 | | | | |
| 431 | 595 | 457 | 587 | | | | |
| 432 | 596 | 458 | 610 | | | | |
| 433 | 593 | 459 | 624 | | | | |
| 460 | 613 | 487 | 586 | | | | |
| 461 | 615 | 488 | 609 | | | | |
| 462 | 626 | 489 | 623 | | | | |
| 463 | 625 | 490 | 612 | | | | |
| 464 | 610 | 491 | 614 | | | | |
| 466 | 680 | 492 | 625 | | | | |
λ_max-values
I claim:
1. The disperse dye of the general formula I
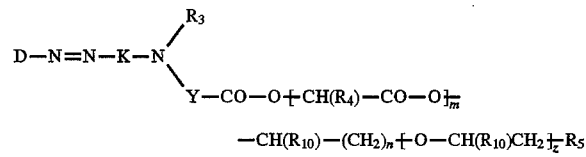
wherein
D signifies a diazo component which is usual with disperse dyes,
K signifies an aromatic radical of formula
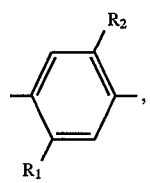 (a)
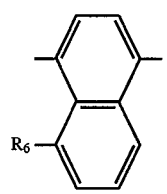 (b)
or

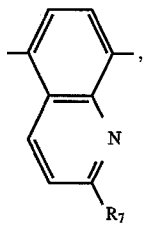

(c)

R₁ signifies hydrogen, chlorine, $C_{1-2}$-alkyl, $C_{1-2}$-alkoxy or acylamino, R₂ signifies hydrogen, $C_{1-4}$-alkoxy, $C_{1-2}$-alkoxyethoxy, chlorine, bromine, or together with R₃ signifies a group of formula —*CH(CH₃)CH₂C(CH₃)₂— (*bonded to the nucleus), R₃ signifies hydrogen, $C_{1-6}$-alkyl, $C_{3-4}$-alkenyl, chloro- or bromo-$C_{3-4}$-alkenyl, $C_{3-4}$-alkinyl, phenyl-$C_{1-3}$-alkyl, $C_{1-4}$-alkoxycarbonyl-$C_{1-3}$-alkyl, $C_{3-4}$-alkenyloxycarbonyl-$C_{1-3}$-alkyl, $C_{3-4}$-alkinyloxycarbonyl-$C_{1-3}$-alkyl, phenoxy-$C_{2-4}$-alkyl; $C_{2-4}$-alkyl substituted by halogen, cyano, $C_{1-4}$-alkoxy, $C_{1-4}$-alkylcarbonyloxy or $C_{1-4}$-alkoxycarbonyloxy; or a group of formula —CH₂—CH(R₈)CH₂—R₉, R₄ signifies hydrogen, phenyl or $C_{1-2}$-alkyl, R₅ signifies a radical of formula

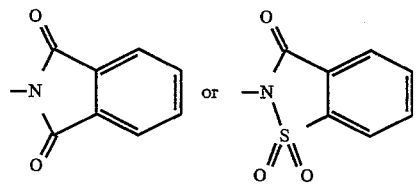

R₇ signifies hydrogen or $C_{1-4}$-alkyl,

R₈ signifies hydroxyl, $C_{1-4}$-alkylcarbonyloxy or $C_{1-4}$-alkylcarbonyloxy, R₉ signifies chlorine, $C_{1-4}$-alkoxy, phenoxy, allyloxy or $C_{1-4}$-alkylcarbonyloxy, R₁₀ signifies hydrogen or $C_{1-4}$-alkyl, Y signifies $C_{2-3}$-alkylene, m and z independently signify zero or 1 and n signifies a number from 1 to 5, whereby, if K is a radical of formula b or c, R₃ only signifies hydrogen, provided that when Y=—CH(CH₃)CH₂—, m=1.

2. The disperse dye according to claim 1, of the general formula Ia

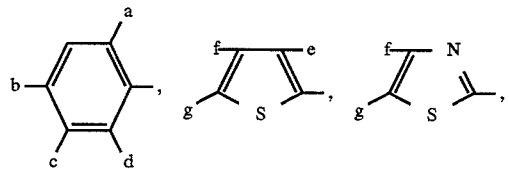

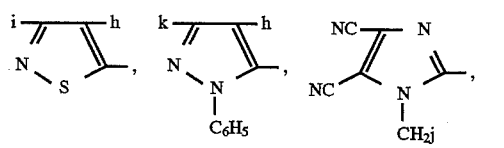

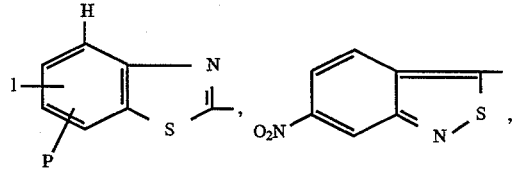

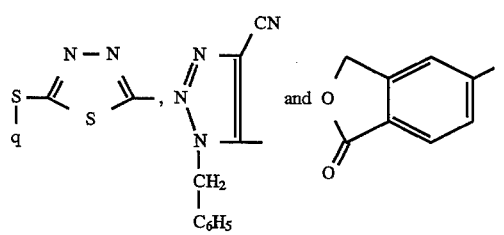

wherein a signifies hydrogen, chlorine, bromine, cyano, nitro-, $C_{1-4}$-alkoxycarbonyl, $C_{1-3}$-alkylsulphonyl, preferably hydrogen, chlorine, cyano or nitro, b signifies chlorine, bromine, nitro, methyl, $C_{1-2}$-alkylsulphonyl, $C_{1-4}$-alkylcarbonyl, aminosulphonyl, mono- or di-$C_{1-4}$-alkylaminosulphonyl, phenylaminosulphonyl, $C_{1-4}$-alkoxycarbonyl, aminocarbonyl, mono- or di-$C_{1-4}$-alkylaminocarbonyl, phenylaminocarbonyl, phenylazo, benzyloxycarbonyl, tetrahydrofurfuryl-2-oxycarbonyl, $C_{3-4}$-alkenyloxycarbonyl, $C_{3-4}$-alkinyloxycarbonyl or phenoxycarbonyl, c signifies hydrogen or chlorine, or if d is hydrogen, also thiocyano, d signifies hydrogen, chlorine, bromine or cyano, (Ia)

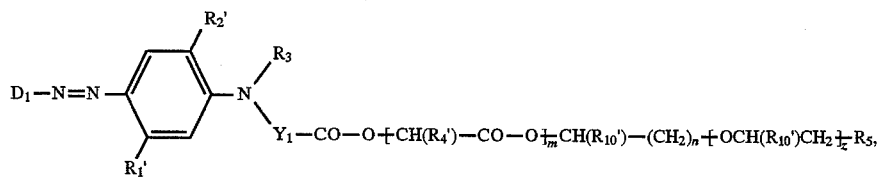

e signifies nitro, $C_{1-4}$-alkylcarbonyl, $C_{1-4}$-alkoxycarbonyl, cyano, aminocarbonyl, mono- or di-$C_{1-2}$-alkylaminocarbonyl, f signifies hydrogen, chlorine, bromine, $C_{1-2}$-alkyl or phenyl, wherein D₁ is 3-phenyl-1,2,4-thiadiazolyl or corresponds to one of the following formulae:

g signifies nitro, cyano, formyl, dicyanovinyl or a group of formula —CH=CH—NO$_2$, —CH=C(CN)CO—OC$_{1-4}$-alkyl, H$_5$C$_6$—N=N— or 3- or 4-NO$_2$—C$_6$H$_4$—N=N—, h signifies cyano or C$_{1-4}$-alkoxycarbonyl, i signifies C$_{1-4}$-alkyl or phenyl, j signifies —CN, —CH=CH$_2$ or phenyl, k signifies C$_{1-4}$-alkyl, l signifies hydrogen, chlorine, bromine, cyano, thiocyano, nitro, C$_{1-4}$-alkoxycarbonyl or di-C$_{1-4}$-alkylaminosulphonyl, p signifies hydrogen, chlorine or bromine and q signifies C$_{1-4}$-alkyl, C$_{1-4}$-alkoxycarbonyl-C$_{1-4}$-alkylene or C$_{1-4}$-alkylene-COOCH$_2$CF$_3$, whereby the phenyl nuclei of these substituents may bear one or two substituents from the series chlorine, bromine, methyl or C$_{1-2}$-alkoxy, R$_1$' signifies hydrogen, C$_{1-2}$-akyl, chlorine or acylamino, R$_2$' signifies hydrogen, chlorine, C$_{1-2}$-alkoxy, C$_{1-2}$-alkoxyethoxy, or with R$_3$, a group of formula —CH(CH$_3$)CH$_2$C(CH$_3$)$_2$—, R$_3$ signifies hydrogen, C$_{1-6}$-alkyl, C$_{3-4}$-alkenyl, chloro- or bromo-C$_{3-4}$-alkenyl, C$_{3-4}$-alkinyl, phenyl-C$_{1-3}$-alkyl, C$_{1-4}$-alkoxycarbonyl-C$_{1-3}$-alkyl, C$_{3-4}$-alkenyloxycarbonyl-C$_{1-3}$-alkyl, C$_{3-4}$-alkinyloxycarbonyl-C$_{1-3}$-alkyl, phenoxy-C$_{2-4}$-alkyl; C$_{2-4}$-alkyl substituted by halogen, cyano, C$_{1-4}$-alkoxy, C$_{1-4}$-alkylcarbonyloxy or C$_{1-4}$-alkoxycarbonyloxy; or a group of formula —CH$_2$—CH(R$_8$)CH$_2$—R$_9$, R$_5$ signifies a radical of formula

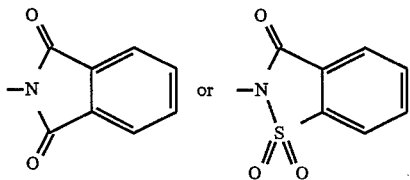

R$_4$' and R$_{10}$' independently signify hydrogen or C$_{1-2}$-alkyl and

Y$_1$ signifies a group of formula —CH$_2$CH$_2$— or —CH(CH$_3$)CH$_2$— m and z independently signify zero or 1 and n signifies a number from 1 to 5 provided that when Y=—CH(CH$_3$)CH$_2$—, m=1.

3. The disperse dye according to claim 2, of formula Ib wherein

D$_2$ signifies the radical of a diazo component from the series 2,6-dicyano-4-chloro-, -4-bromo-, -4-methyl- or -4-nitrophenyl, 2,4-dinitro-6-chloro-, -6-bromo- or -6-cyanophenyl, 2-chloro- or 2-bromo-4-nitro-6-cyanophenyl, 2,4-dinitrophenyl, 2,6-dichloro or 2,6-dibromo-4-nitrophenyl, 2-chloro-4-nitro-6-bromophenyl, 2-chloro-, 2-bromo- or 2-cyano-4-nitrophenyl, 2,4-dinitro-5-chlorophenyl or -5-thiocyanophenyl, 2,4-dinitro-5,6-dichlorophenyl, 2,5-dichloro-4-nitrophenyl, 4-nitrophenyl, 4-phenylazophenyl, 4-C$_{3-4}$-alkenyloxycarbonylphenyl, 4-C$_{3-4}$-alkinyloxycarbonylphenyl, 4-C$_{1-4}$-alkoxycarbonylphenyl, 2-C$_{1-4}$-alkoxycarbonyl-4-nitrophenyl, 4-phenoxycarbonylphenyl, 4-benzyloxycarbonylphenyl, 4-(tetrahydrofurfuryl-2'-oxycarbonyl)-phenyl, 3,5-dicyano-4-chloro-thienyl-2, 3,5-dicyano-thienyl-2, 3-cyano-5-nitro-thienyl-2, 3-acetyl-5-nitro-thienyl-2, 3,5-dinitro-thienyl-2, 3-(C$_{1-4}$-alkoxycarbonyl)-5-nitro-thienyl-2, 5-phenylazo-3-cyanothienyl-2, 5-phenylazo-3-cyano-4-methyl-thienyl-2, 5-nitro-thiazolyl-2, 5-nitrobenzisothiazolyl-3, 3-methyl-4-cyano-isothiazolyl-5, 3-phenyl-1,2,4-thiadiazolyl-2, 5-(C$_{1-2}$-alkylmercapto)-1,3,4-thiadiazolyl-2, 3-C$_{1-2}$-alkoxycarbonylethylmercapto-1,2,4-thiadiazolyl-5, 1-cyanomethyl-4,5-dicyanoimidazolyl-2, 6-nitrobenzothiazolyl-2, 5-nitrobenzothiazolyl-2, 6-thiocyanobenzothiazolyl-2, 6-chlorobenzothiazolyl-2, (5),6,(7)-dichlorobenzothiazolyl-2,

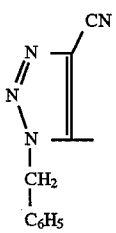

or of formula

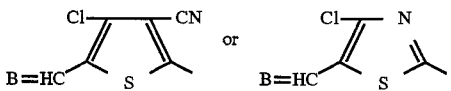

(Ib)

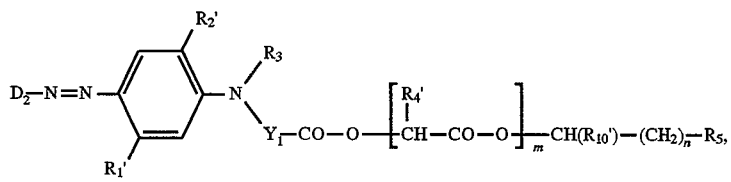

and B signifies oxygen or a group of formula

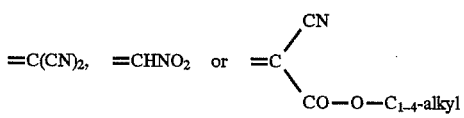

$R_1'$ signifies hydrogen, $C_{1-2}$-alkyl, chlorine or acylamino, $R_2'$ signifies hydrogen, chlorine, $C_{1-2}$-alkoxy, $C_{1-2}$-alkoxyethoxy, or with $R_3$, a group of formula —CH($CH_3$)$CH_2$C($CH_3$)$_2$—, $R_3$ signifies hydrogen, $C_{1-6}$-alkyl, $C_{3-4}$-alkenyl, chloro- or bromo-$C_{3-4}$-alkenyl, $C_{3-4}$-alkinyl, phenyl-$C_{1-3}$-alkyl, $C_{1-4}$-alkoxycarbonyl-$C_{1-3}$-alkyl, $C_{3-4}$-alkenyloxycarbonyl-$C_{1-3}$-alkyl, $C_{3-4}$-alkinyloxycarbonyl-$C_{1-3}$-alkyl, phenoxy-$C_{2-4}$-alkyl; $C_{2-4}$-alkyl substituted by halogen, cyano, $C_{1-4}$-alkoxy, $C_{1-4}$-alkylcarbonyloxy or $C_{1-4}$-alkoxycarbonyloxy; or a group of formula —$CH_2$—CH($R_8$)$CH_2$—$R_9$, $R_5$ signifies a radical of formula

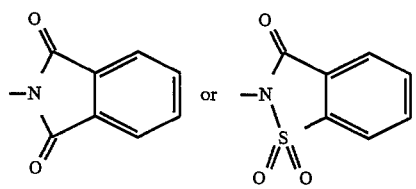

$R_4'$ and $R_{10}'$ independently signify hydrogen or $C_{1-2}$-alkyl and $Y_1$ signifies a group of formula —$CH_2CH_2$— or —CH($CH_3$)$CH_2$— m and z independently signify zero or 1 and n signifies a number from 1 to 5.

4. The disperse dye according to claim 3, wherein $D_2$ signifies the radical of a diazo component from the series 2,6-dicyano-4-chloro, -4-bromo, -4-methyl or -4-nitrophenyl, 2,4-dinitro-6-chloro-, -6-bromo- or -6-cyanophenyl, 2-chloro- or 2-bromo-4-nitro-6-cyanophenyl, 2,4-dinitrophenyl, 2,6-dichloro- or 2,6-dibromo-4-nitrophenyl, 2-chloro-4-nitro-6-bromophenyl, 2-chloro-, 2-bromo- or 2-cyano-4-nitrophenyl, 2,4-dinitro-5-chlorophenyl or -5-thiocyanophenyl, 2,4-dinitro-5,6-dichlorophenyl, 2,5-dichloro-4-nitrophenyl, 4-nitrophenyl, phthalidyl-5 or of formula

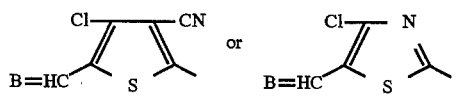

and B signifies oxygen or a group of formula

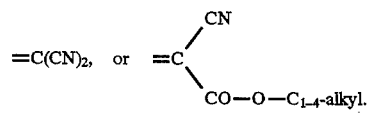

5. The disperse dye of the general formula Ib according to claim 3, wherein $D_2$ signifies a diazo component from the series 2,4-dinitro-6-chloro-, -6-bromo- or -6-cyanophenyl, 2,4-dinitro-5-chloro- or -5-thiocyanophenyl or 2,4-dinitro-5,6-dichlorophenyl, $R_1'$ signifies $C_{1-2}$-alkylcarbonylamino, $R_2'$ signifies $C_{1-2}$-alkoxy or $C_{1-2}$-alkoxyethoxy, $R_3$ signifies hydrogen, $C_{1-4}$-alkyl, cyanoethyl, $C_{1-2}$-alkoxyethyl, $C_{3-4}$-alkenyl, chlorallyl, $C_{3-4}$-alkinyl, $C_{1-2}$-alkoxycarbonylmethyl, allyloxycarbonylmethyl or propargyloxycarbonylmethyl, $R_4'$ signifies hydrogen or methyl, $R_5$ signifies a radical of formula

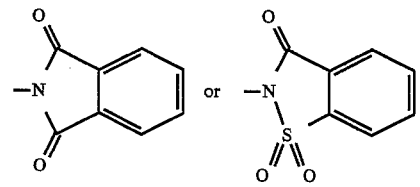

$R_{10}'$ signifies hydrogen or methyl, $Y_1$ signifies a group of formula —$CH_2CH_2$— or —CH($CH_3$)$CH_2$— m signifies zero or 1 and n signifies a number from 1 to 5.

6. The disperse dye of formula Ib, according to claim 3, wherein $D_2$ signifies a diazo component from the series 2,4-dinitro-6-chloro- or -6-bromophenyl, $R_1'$ signifies $C_{1-2}$-alkylcarbonylamino, $R_2'$ signifies methoxy or ethoxy, $R_3$ signifies hydrogen, allyl, chlorallyl or propargyl, R$_5$ signifies a radical of formula

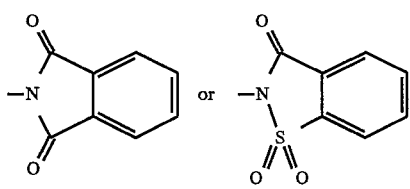

R$_4$' and R$_{10}$' independently signify hydrogen or methyl,

Y$_1$ signifies 1,2-ethylene, m signifies zero or 1, and n signifies a number from 1 to 5.

7. The disperse dye of formula I, according to claim 1, wherein

D signifies a diazo component from the series 4-nitrophenyl, 4-nitro-2-ethylsulphonylphenyl, 4-nitro-2-methylsulphonylphenyl, 4-methoxycarbonylphenyl, phthalidyl-5, 4-ethoxycarbonylphenyl, 2-chloro-4-nitrophenyl, 2,6-dichloro-4-nitrophenyl, 2-bromo-4-nitro-6-chlorophenyl or 2-cyano-4-nitrophenyl, K signifies a radical of formula a R$_1$ signifies hydrogen, methyl, acylamino or chlorine, R$_2$ signifies hydrogen, R$_3$ signifies C$_{1-4}$-alkyl, C$_{3-4}$-alkenyl, chlorallyl, benzyl, cyanoethyl, C$_{1-2}$-alkoxyethyl, C$_{1-4}$-alkylcarbonyloxyethyl, C$_{1-2}$-alkoxycarbonylethyl or C$_{1-4}$-alkoxycarbonyloxyethyl, R$_4$ and R$_{10}$ independently signify hydrogen or C$_{1-2}$-alkyl, R$_5$ signifies a radical of formula

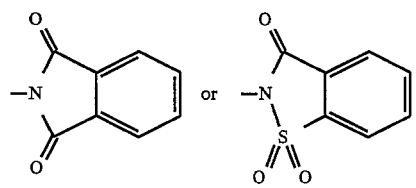

Y signifies a group of formula —CH$_2$CH$_2$— or —CH(CH$_3$)CH$_2$— m and z independently signify zero or 1, and n signifies a number from 1 to 5.

8. The disperse dye of formula Ib, according to claim 3, wherein

D$_2$ signifies a diazo component from the series 4-nitrophenyl, 2-chloro-4-nitrophenyl, 2-bromo-4-nitrophenyl, 2,6-dichloro-4-nitrophenyl, 2-chloro4-nitro-6-bromophenyl, 2-cyano-4-nitrophenyl, R$_1$' signifies hydrogen or methyl, R$_2$' signifies hydrogen, R$_3$ signifies C$_{1-4}$-alkyl, R$_4$' signifies hydrogen or methyl, R$_5$ signifies a radical of formula

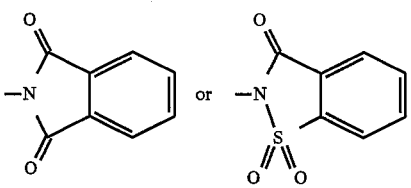

R$_{10}$' signifies hydrogen,

Y$_1$ signifies 1,2-ethylene, m signifies zero or 1, and n signifies the number 1.

9. Process for the production of the disperse dyes of formula I, according to claim 1, characterized in that a diazotised amine of formula II

is coupled with a compound of formula III

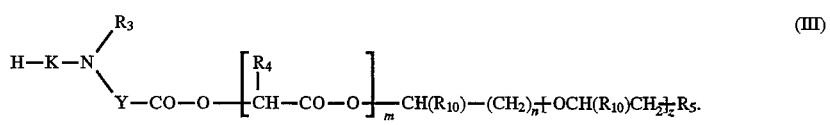

10. A process for dyeing or printing a substrate comprising applying to the substrate a compound according to claim 1.

11. A process according to claim 10 wherein the substrate is a fibre, filament or a material produced therefrom.

12. A process according to claim 11 wherein the substrate is a fully synthetic or semi-synthetic, hydrophobic, high-molecular weight material.

13. A process according to claim 10 wherein the substrate is a textile material consisting of linear, aromatic polyesters, cellulose-2½-acetate, cellulose triacetate or a combination thereof.

14. A process for thermo transfer printing comprising thermo transferring to a substrate a compound according to claim 1.

* * * * *